(12) United States Patent
Ohkuma

(10) Patent No.: US 6,848,439 B2
(45) Date of Patent: Feb. 1, 2005

(54) AIR-FUEL RATIO CONTROL APPARATUS, AIR-FUEL RATIO DETECTING APPARATUS AND METHODS THEREOF FOR ENGINE

(75) Inventor: Shigeo Ohkuma, Atsugi (JP)

(73) Assignee: Hitachi Unisia Automotive, Ltd., Atsugi (JP)

( * ) Notice: Subject to any disclaimer, the term of this patent is extended or adjusted under 35 U.S.C. 154(b) by 81 days.

(21) Appl. No.: 10/290,356

(22) Filed: Nov. 8, 2002

(65) Prior Publication Data

US 2003/0084892 A1 May 8, 2003

(30) Foreign Application Priority Data

Nov. 8, 2001 (JP) ........................................ 2001-343758
Nov. 19, 2001 (JP) ........................................ 2001-353242

(51) Int. Cl.[7] .............................................. F02D 41/14
(52) U.S. Cl. ...................... 123/688; 123/697; 123/698; 60/276
(58) Field of Search ................................. 123/688, 697, 123/698; 60/276

(56) References Cited

U.S. PATENT DOCUMENTS

| | | | | |
|---|---|---|---|---|
| 5,353,774 A | * | 10/1994 | Furuya | 123/697 |
| 5,616,835 A | * | 4/1997 | Schnaibel et al. | 123/697 |
| 5,771,688 A | * | 6/1998 | Hasegawa et al. | 60/276 |
| 6,116,021 A | * | 9/2000 | Schumacher et al. | 60/276 |
| 6,304,813 B1 | * | 10/2001 | Ikeda et al. | 123/697 |
| 6,343,499 B1 | * | 2/2002 | Inagaki et al. | 123/688 |
| 6,347,544 B1 | * | 2/2002 | Hada et al. | 123/697 |
| 6,541,741 B2 | * | 4/2003 | Ikeda | 123/697 |
| 2001/0008990 A1 | * | 7/2001 | Ishii et al. | 60/276 |

FOREIGN PATENT DOCUMENTS

| | | |
|---|---|---|
| JP | 7-127505 A | 5/1995 |
| JP | 11-229930 A | 8/1999 |

* cited by examiner

Primary Examiner—Erick Solis
(74) Attorney, Agent, or Firm—Foley & Lardner LLP

(57) ABSTRACT

In a constitution for feedback controlling an air-fuel ratio using an oxygen concentration detector in which a detection signal thereof has a linearity to the air-fuel ratio within a predetermined air-fuel ratio range inclusive of a stoichiometric air-fuel ratio, when the detection signal from the oxygen concentration detector is outside a region indicating the linearity, a change in air-fuel ratio feedback control signal is limited to be smaller than that when the detection signal from the oxygen concentration detector is within the region indicating the linearity.

24 Claims, 18 Drawing Sheets

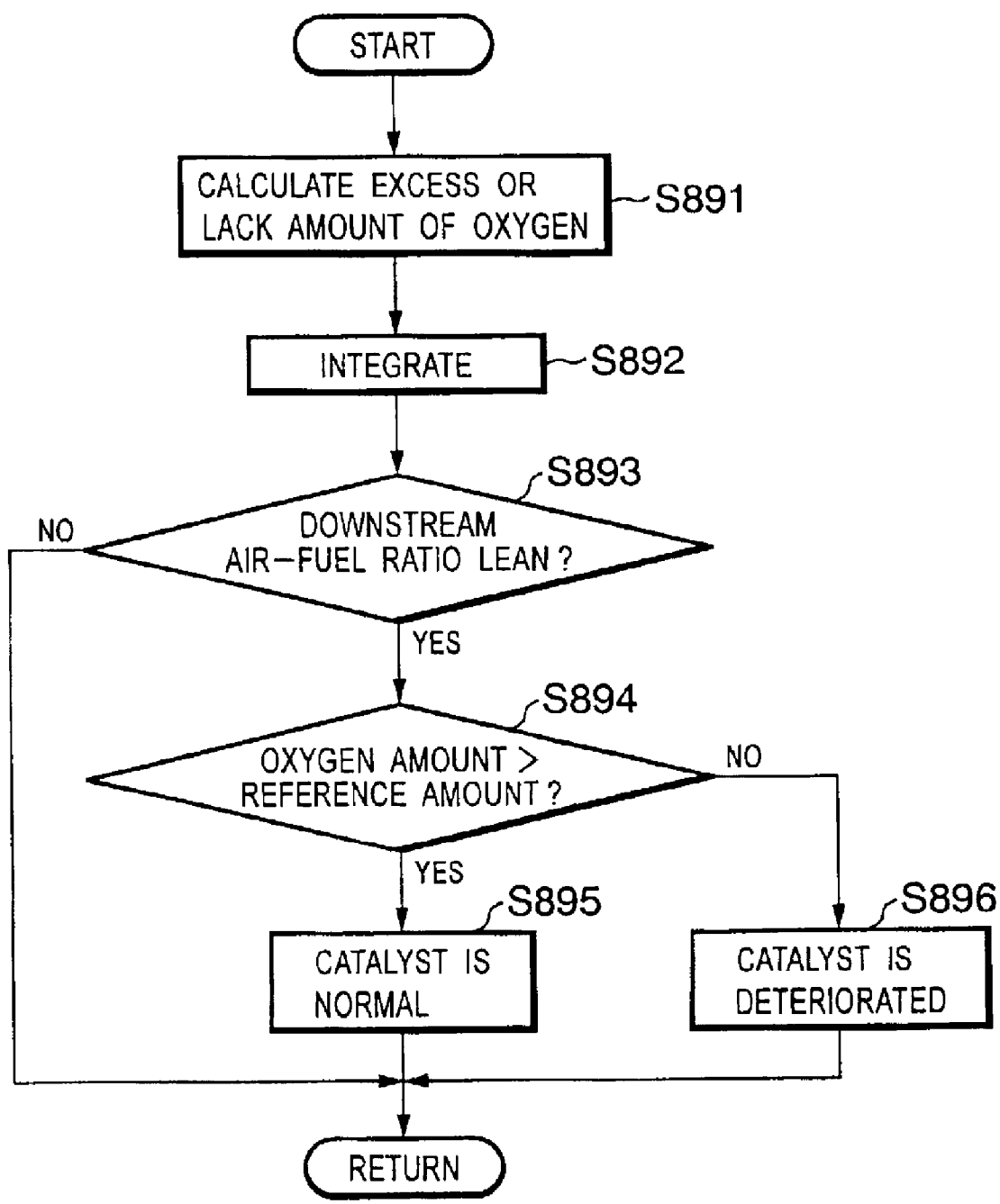

AIR-FUEL RATIO CONTROL APPARATUS, AIR-FUEL RATIO DETECTING APPARATUS AND METHODS THEREOF FOR ENGINE

FIELD OF THE INVENTION

The present invention relates to a technology for detecting an air-fuel ratio using an oxygen concentration detector detecting oxygen concentration in engine exhaust air, and for feedback controlling an air-fuel ratio based on the detected air-fuel ratio.

RELATED ART

Heretofore, there has been known an air-fuel ratio control apparatus for detecting an air-fuel ratio of an engine combustion mixture in a wide range based on an output of an oxygen sensor of oxygen concentration cell type, and for feedback controlling an air-fuel ratio control signal based on a deviation between the detected actual air-fuel ratio and a target air-fuel ratio (refer to Japanese Unexamined Patent Publication No. 7-127505).

Generally, such an oxygen sensor of oxygen concentration cell type exhibits a characteristic in which an electromotive force thereof is abruptly changed on reaching a stoichiometric air-fuel ratio.

Therefore, even in the case where, in order to enable to detect the air-fuel ratio in a wide range, compositions and the like of an element are adjusted so that an output characteristic exhibits linearity, a linear region is limited to a narrow region in the vicinity of the stoichiometric air-fuel ratio.

Consequently, the air-fuel ratio can be detected with high accuracy within the linear region. However, there is a problem in that, if the electromotive force of the oxygen sensor is outside the linear region, detection accuracy of air-fuel ratio is reduced to lower convergence stability in an air-fuel ratio feedback control.

Further, even in the case where the compositions and the like of the element are adjusted so that the output characteristic of the oxygen sensor of oxygen concentration cell type exhibits the linearity, such a characteristic can only be achieved in a condition of high element temperature (700 to 800° C.).

Consequently, there is a problem in that, since it is needed a time until a characteristic capable of detecting the air-fuel ratio in a wide range after engine start is achieved, if the air-fuel ratio feedback control is stopped during this period, exhaust emission immediately after engine start is deteriorated.

Moreover, in the case where a heater is used to accelerate the rise of element temperature, if the sensor element is abruptly heated by the heater when a water is adhered to the element immediately after engine start, cracking or the like of element is often caused due to thermal shock.

Here, there is a case where, as an engine air-fuel ratio detection request, it is satisfactory to detect the air-fuel ratio in a wide range only under a limited condition. Further, since the oxygen sensor of oxygen concentration cell type exhibits the characteristic in which the output thereof is abruptly changed on reaching the stoichiometric air-fuel ratio under a condition of low element temperature (300 to 400° C.), it is possible to detect rich/lean of the air-fuel ratio to the stoichiometric air-fuel ratio.

SUMMARY OF THE INVENTION

Therefore, an object of the present invention is for enabling to maintain convergence stability of an air-fuel ratio feedback control, even if an air-fuel ratio is greatly deviated from the vicinity of a stoichiometric air-fuel ratio.

A further object of the present invention is for enabling to appropriately switch a detection characteristic of an oxygen concentration detector between a characteristic capable of detecting the air-fuel ratio in a wide range and a characteristic capable of only rich/lean judging, to improve reduction of electric power consumption and air-fuel ratio feedback controllability.

In order to achieve the above objects, the present invention is constituted so that when a detection signal of an oxygen concentration detector is outside a region indicating linearity to an air-fuel ratio, a change in an air-fuel ratio feedback control signal is limited to be smaller than that when the detection signal of the oxygen concentration detector is within the region.

Further, the present invention is constituted so that, by controlling a heater that heats an element of the oxygen concentration detector, an element temperature is switched to either a first temperature region where the detection signal is abruptly changed on reaching a stoichiometric air-fuel ratio, or a second temperature region where the detection signal indicates the linearity to the air-fuel ratio in a predetermined air-fuel ratio range inclusive of the stoichiometric air-fuel ratio.

The other objects and features of this invention will become understood from the following description with reference to the accompanying drawings.

BRIEF EXPLANATION OF THE DRAWINGS

FIG. 19 is a flowchart showing the detail of catalyst diagnosis.

DETAILED DESCRIPTION OF THE INVENTION

Figure 1:
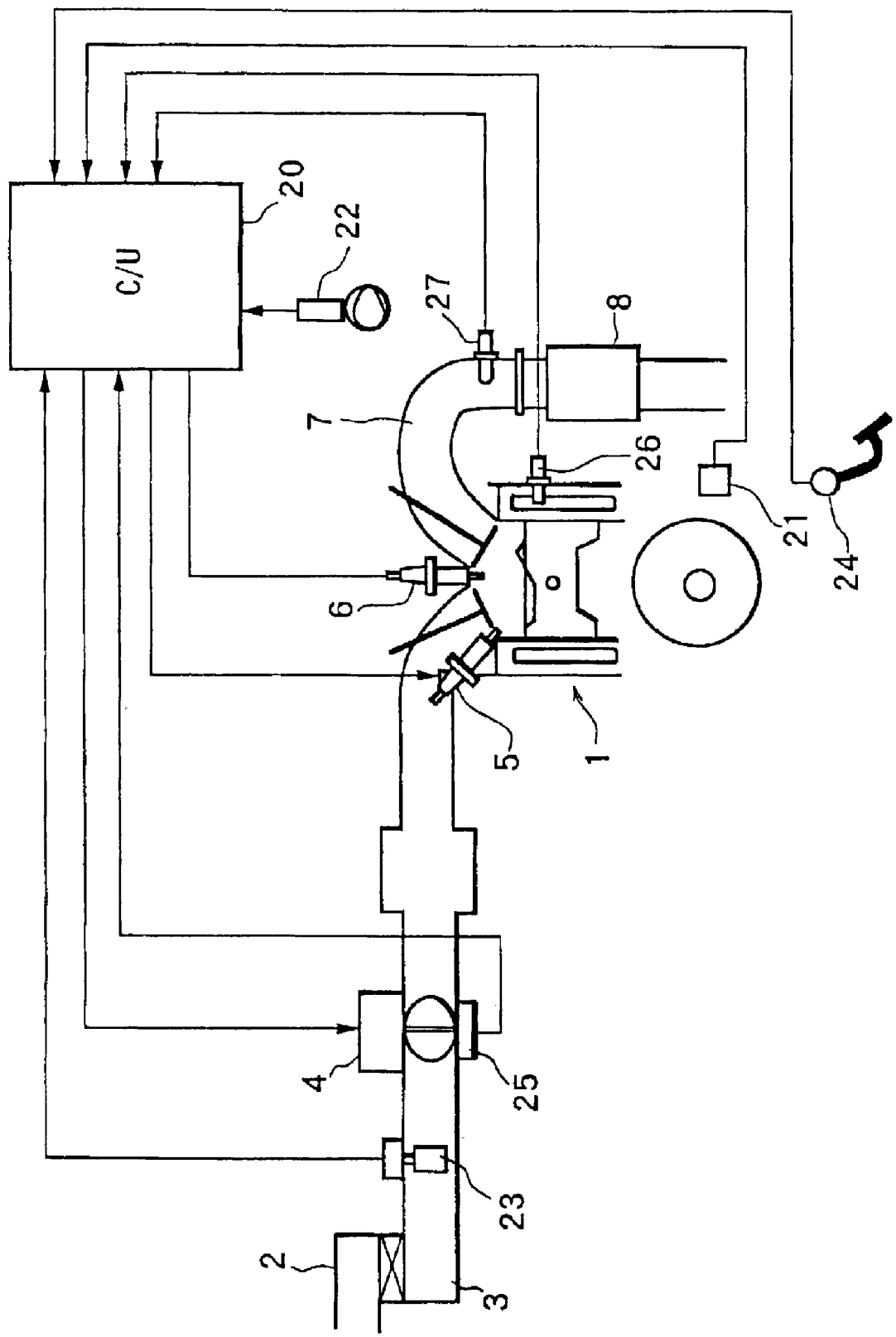
FIG. 1 is a diagram showing a system structure of an engine.

FIG. 1 is diagram showing an entire system structure of an engine.

In FIG. 1, air is sucked into a combustion chamber of each cylinder of an engine 1 installed on a vehicle, via an air cleaner 2, an intake pipe 3, and an electronically controlled throttle valve 4.

There is provided an electromagnetic fuel injection valve 5 directly injecting fuel (gasoline) into the combustion chamber of each cylinder.

In the combustion chamber, an air-fuel mixture is formed of fuel injected by fuel injection valve 5 and intake air.

Fuel injection valve 5 is opened by an injection pulse signal output from a control unit 20, to inject fuel adjusted at a predetermined pressure.

The air-fuel mixture formed in the combustion chamber is ignited to burn by an ignition plug 6.

Note, engine 1 is not limited to a direct injection type gasoline engine, and may be an engine configured to inject fuel to an intake port.

An exhaust gas from engine 1 is discharged from an exhaust pipe 7.

An exhaust purification catalyst 8 is disposed to exhaust pipe 7.

Catalyst 8 is a three-way catalyst having a capability to store oxygen.

This three-way catalyst oxidizes carbon monoxide CO and hydrocarbon HC, and reduces nitrogen oxide NOx, harmful three components, to convert them to harmless carbon dioxide, water vapor and nitrogen.

Purification performance of three-way catalyst 8 is highest when an exhaust air-fuel ratio equals to a stoichiometric air-fuel ratio. If the exhaust air-fuel ratio is lean and an oxygen amount is excessive, oxidization by three-way catalyst 8 becomes active but reduction thereby becomes inactive, on the contrary, the exhaust air-fuel ratio is rich and the oxygen amount is less, the oxidization becomes inactive but the reduction becomes active.

However, since three-way catalyst 8 has the capability to store oxygen, when the exhaust air-fuel ratio becomes temporarily rich, carbon monoxide CO and hydrocarbon HC are oxidized using the oxygen stored up to that time, on the contrary, when the exhaust air-fuel ratio becomes temporarily lean, nitrogen oxide NOx is reduced by storing excess oxygen.

Accordingly, if an amount of oxygen to be stored in three-way catalyst 8 is maintained at around the half of maximum amount capable to be stored, it is possible to achieve a state where an excess amount of oxygen is stored, and oxygen necessary for oxidizing process can be eliminated and supplied.

Therefore, when a predetermined air-fuel ratio feedback control condition is established, control unit 20 feedback controls a fuel injection quantity by fuel injection valve 5 so as to coincide a stored oxygen amount in three-way catalyst 8 with a target amount.

The target amount is around the half of the maximum stored oxygen amount in three-way catalyst 8.

Control unit 20 incorporates therein a microcomputer including a CPU, a ROM, a RAM, an A/D converter, an input/output interface and the like.

Control unit 20 receives detection signals output from various sensors, and controls a throttle opening of electronically controlled throttle valve 4, the injection quantity and injection timing of fuel injection valve 5, and ignition timing of ignition plug 6, based on these detection signals.

As one of the various sensors, there are disposed a crank angle sensor 21 detecting a crank angle of engine 1, and a cam sensor 22 taking out a cylinder discrimination signal from a camshaft.

Other than the above, there are disposed an air flow meter 23 detecting an intake air amount Q at an upstream side of electronically controlled throttle valve 4, an accelerator sensor 24 detecting a depression amount APS of accelerator pedal, a throttle sensor 25 detecting a throttle opening TVO in electronically controlled throttle valve 4, and a water temperature sensor 26 detecting a cooling water temperature.

On an upstream side of catalyst 8, there is disposed an oxygen sensor 27 of oxygen concentration cell type that generates an electromotive force according to a ratio between oxygen concentration in engine exhaust and oxygen concentration in the atmosphere.

In oxygen sensor 27, compositions of element thereof or manufacturing method thereof are adjusted so that the electromotive force (detection signal) has linearity to an air-fuel ratio within a predetermined air-fuel ratio range inclusive of a stoichiometric air-fuel ratio.

Control unit 20 detects the air-fuel ratio by converting the electromotive force of oxygen sensor 27 to data of air-fuel ratio, and estimates the stored oxygen amount in three-way catalyst 8 based on the detected air-fuel ratio.

Here, an air-fuel ratio feedback control by control unit 20 will be described in accordance with a block diagram in FIG. 3.

Figure 3:
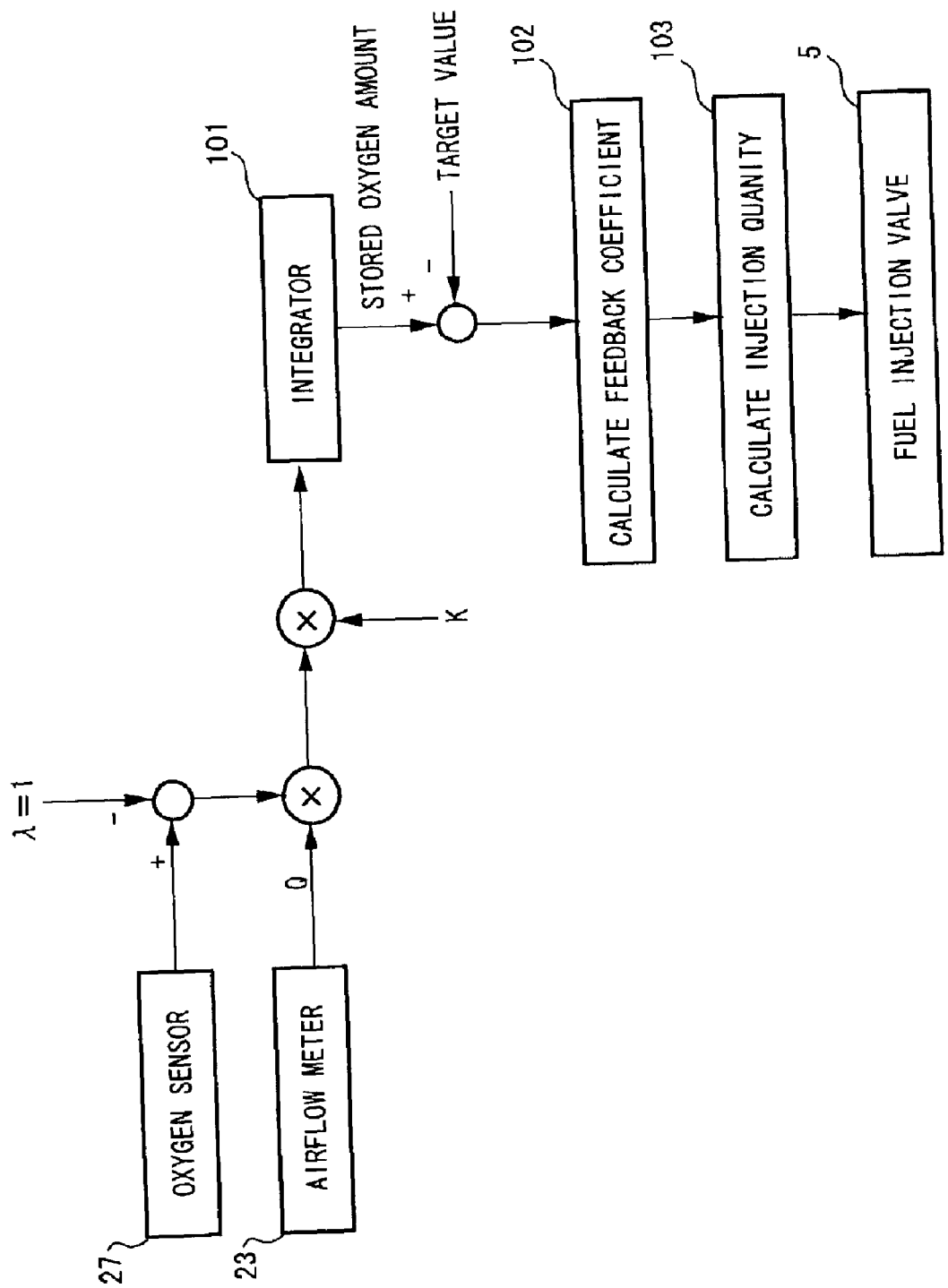
FIG. 3 is a block diagram showing an entire constitution of an air-fuel ratio feedback control based on estimation of a stored oxygen amount.

In the block diagram in FIG. 3, the intake air amount Q detected by air flow meter 23 is multiplied by a deviation $\Delta\lambda$ between the stoichiometric air-fuel ratio (excess air ratio $\lambda=1$) and an excess air ratio obtained based on the electromotive force of oxygen sensor 27.

The intake air amount Q corresponds to an exhaust gas amount.

The deviation $\Delta\lambda$ becomes a positive value if the air-fuel ratio of combustion mixture is leaner than the stoichiometric air-fuel ratio, while becomes a negative value if the air-fuel ratio of combustion mixture is richer than the stoichiometric air-fuel ratio.

Such a positive/negative change of $\Delta\lambda$ corresponds to the fact that, if the air-fuel ratio of combustion mixture is leaner than the stoichiometric air-fuel ratio, the stored oxygen amount in catalyst 8 is changed to increase, while if the air-fuel ratio of combustion mixture is richer than the stoichiometric air-fuel ratio, the stored oxygen amount in catalyst 8 is changed to decrease.

A multiplication result of the intake air amount Q and the deviation $\Delta\lambda$ is further multiplied by a constant K, to obtain an oxygen amount flowing into the catalyst 8. In an integrator 101, this oxygen amount is sequentially integrated, to obtain the stored oxygen amount in catalyst 8.

Next, a deviation between the stored oxygen amount output from integrator 101 and a target value is calculated.

In an air-fuel ratio feedback correction coefficient setting section 102, an air-fuel ratio feedback correction coefficient (an air-fuel ratio feedback control signal) for correcting the fuel injection quantity is calculated, so that the estimated value of the stored oxygen amount coincides with the target value.

That is, when the stored oxygen amount is less than a target amount, the air-fuel ratio is made leaner to increase the stored oxygen amount, while when the stored oxygen amount is larger than the target amount, the air-fuel ratio is made richer to eliminate the excess oxygen, to decrease the stored oxygen amount.

In an injection quantity calculating section 103, a basic fuel injection quantity is corrected using the air-fuel ratio feedback correction coefficient to calculate a final fuel injection quantity, and the injection pulse signal corresponding to the fuel injection quantity is output to fuel injection valve 5 at predetermined timing.

Figure 4:
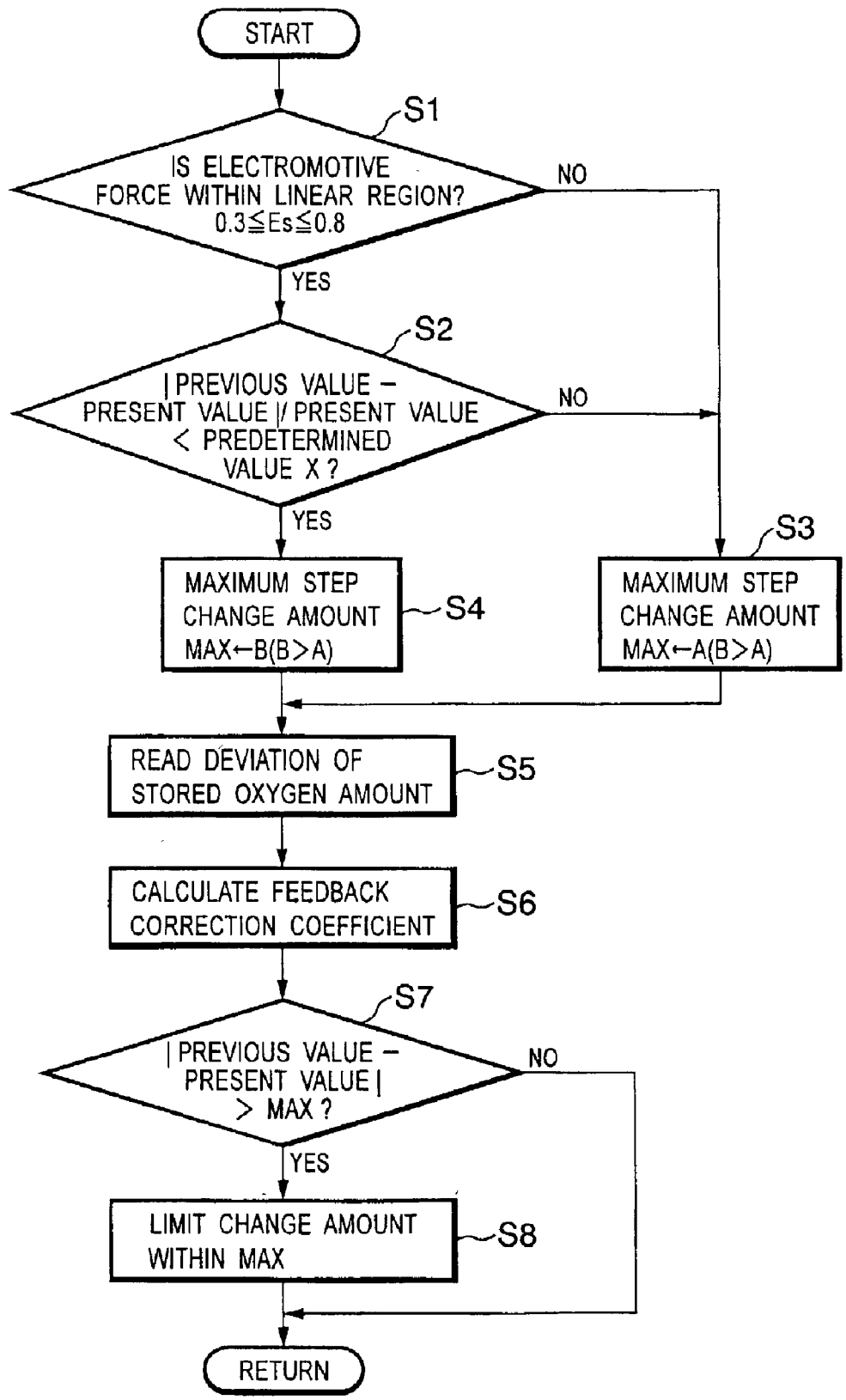
FIG. 4 is a flowchart showing a first embodiment of feedback correction coefficient calculation.

A flowchart in FIG. 4 shows the detail of control contents in air-fuel ratio feedback correction coefficient setting section 102.

At step S1, it is judged whether or not an electromotive force Es of oxygen sensor 27 is within a linear region.

Figure 2:
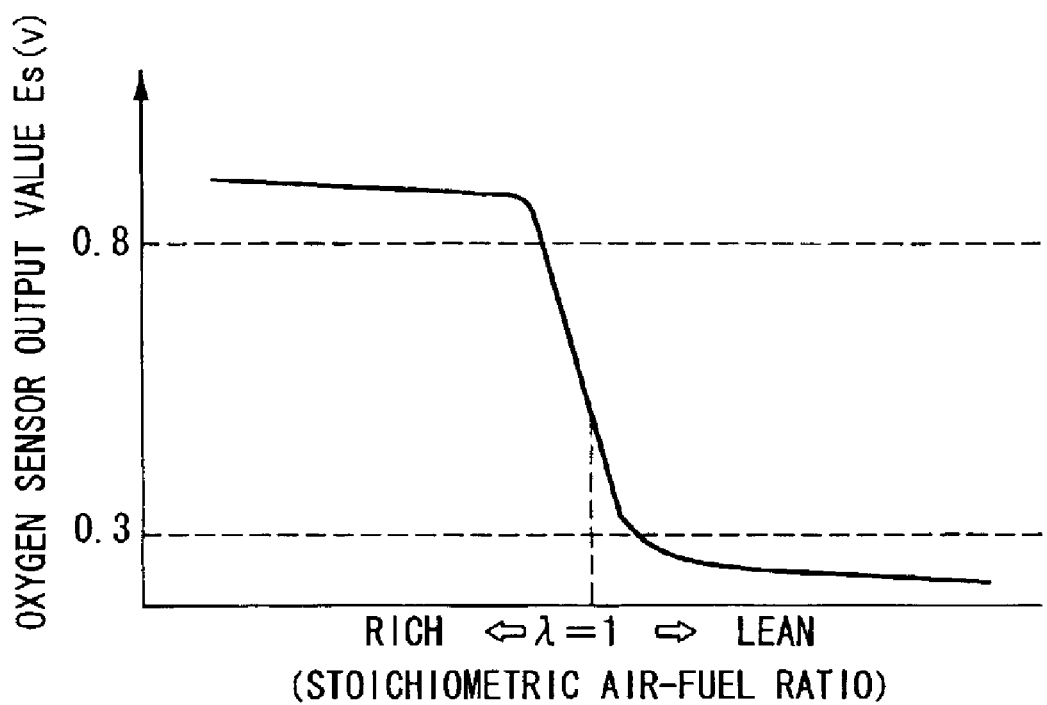
FIG. 2 is a graph showing an output characteristic of an oxygen sensor.

For example, if oxygen sensor 27 has the output characteristic as shown in FIG. 2 and a range of from 0.3V to 0.8V is the linear region, it is judged that the sensor electromotive force Es is within the linear region when $0.3V \leq Es \leq 0.8V$.

If the electromotive force Es of oxygen sensor 27 is outside the linear region, control proceeds to step S3.

At step S3, a predetermined value A is set to a maximum step change amount MAX of the feedback correction coefficient.

On the other hand, if it is judged that the electromotive force Es of oxygen sensor 27 is within the linear region, control proceeds to step S2.

At step S2, a change speed of the electromotive force Es of oxygen sensor 27 is calculated in accordance with the following equation;

change speed=|previous value−present value|/present value, to judge whether or not the change speed is smaller than a predetermined value X.

If the change speed is smaller than the predetermined value X, it is judged that the electromotive force Es is stabled within the linear region, and control proceeds to step S4.

At step S4, a predetermined value B is set to the maximum step change amount MAX.

The predetermined value B is a value larger than the predetermined value A, and a larger step change of feedback correction coefficient is permitted when the electromotive force Es is stabled within the linear region compared to the time when the electromotive force Es is outside of the linear region.

On the other hand, if the change speed is equal to or larger than the predetermined value X, it is judged there is a high possibility that, although the electromotive force Es is currently within the linear region, it will be displaced to the outside of the linear region, then control proceeds to step S3.

At step S5, the deviation between the estimated value of the stored oxygen amount and the target value is read in.

At step S6, the air-fuel ratio feedback correction coefficient is calculated by a proportional integral and derivative control based on the deviation of the stored oxygen amount.

Note, the air-fuel ratio feedback correction coefficient can also be calculated by a sliding mode control, other than the proportional integral and derivative control.

At step S7, it is judged whether or not an absolute value of a deviation between a present value and a previous value of the air-fuel ratio feedback correction coefficient exceeds the maximum step change amount MAX.

If the step change amount of the air-fuel ratio feedback correction coefficient exceeds the maximum step change amount MAX, control proceeds to step S8.

At step S8, the air-fuel ratio feedback correction coefficient at which the step change amount from the previous value coincides with the maximum step change amount MAX, is set.

Here, the maximum step change amount MAX is limited to be smaller when the electromotive force of oxygen sensor 27 is outside the linear region and when the electromotive force will be displaced to the outside of the linear region although it is currently within the linear region, compared to the time when it is stabled in the linear region.

If the electromotive force of oxygen sensor 27 is outside the linear region, since the detection accuracy of air-fuel ratio is reduced, the step change amount of the air-fuel ratio feedback correction coefficient is limited to be smaller so that enlargement of error or occurrence of overshoot can be avoided, to thereby suppress deterioration of exhaust emission.

In the above embodiment, the constitution has been such that the step change amount of the air-fuel ratio feedback correction coefficient is limited to be smaller when the electromotive force is outside the linear region. However, the similar function and effect can be achieved by modifying a gain of air-fuel ratio feedback correction coefficient.

Figure 5:
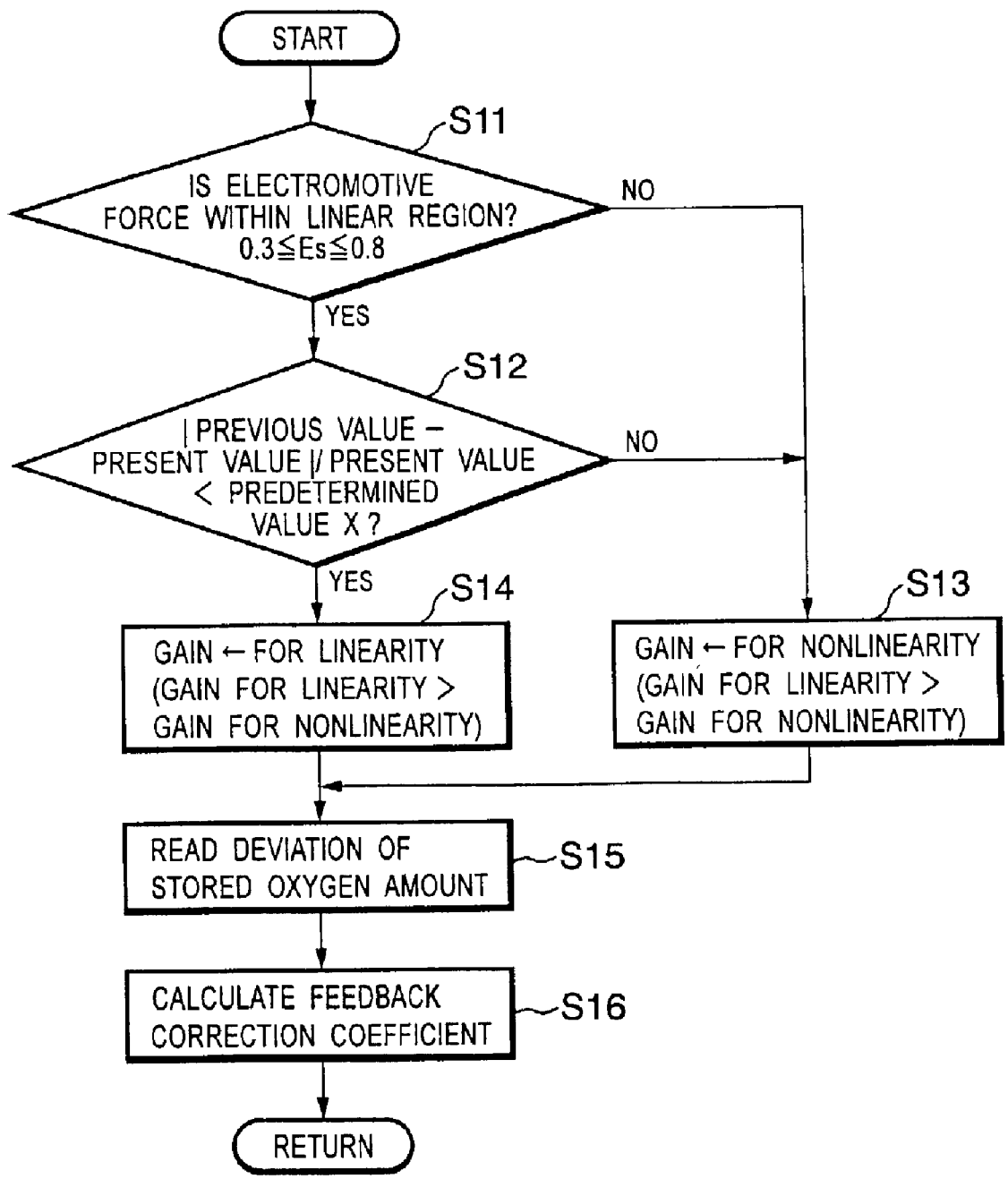
FIG. 5 is a flowchart showing a second embodiment of feedback correction coefficient calculation.

A flowchart of FIG. 5 shows an embodiment in which the gain is modified.

In the flowchart of FIG. 5, at steps S11 and S12, similar to steps S1 and S2, it is judged whether or not the electromotive force Es of oxygen sensor 27 is within the linear region, and if within the linear region, it is also judged whether or not the electromotive force Es is stabled within the linear region.

If the electromotive force of oxygen sensor 27 is outside the linear region and if there is a high possibility that the electromotive force will be displaced to the outside of the linear region although it is currently within the linear region, control proceeds to step S13.

At step S13, as a control gain of the air-fuel ratio feedback correction coefficient, a gain adapted to the time when the electromotive force is outside the linear region, is set.

On the other hand, if the electromotive force Es of oxygen sensor 27 is within the linear region and also stabled within it, control proceeds to step S14.

At step S14, as the control gain of the air-fuel ratio feedback correction coefficient, a gain adapted to the time when the electromotive force is within the linear region, is set.

Then, at step S15, an error of the stored oxygen amount is read in, and at step S16, the air-fuel ratio feedback correction coefficient is calculated using the gain set at step S13 or at step S14.

Here, the gain used for when the electromotive force is outside the linear region, is set to be smaller than the gain used for when the electromotive force is within the linear region.

Accordingly, the air-fuel ratio feedback control is performed using the small gain when the electromotive force is outside the linear region, at which the air-fuel ratio detection accuracy is reduced, thereby enabling to suppress an influence of air-fuel ratio detection error.

Note, the constitution may be such that any one or a plurality of proportional gain, integral gain and derivative gain is modified.

Figure 6:
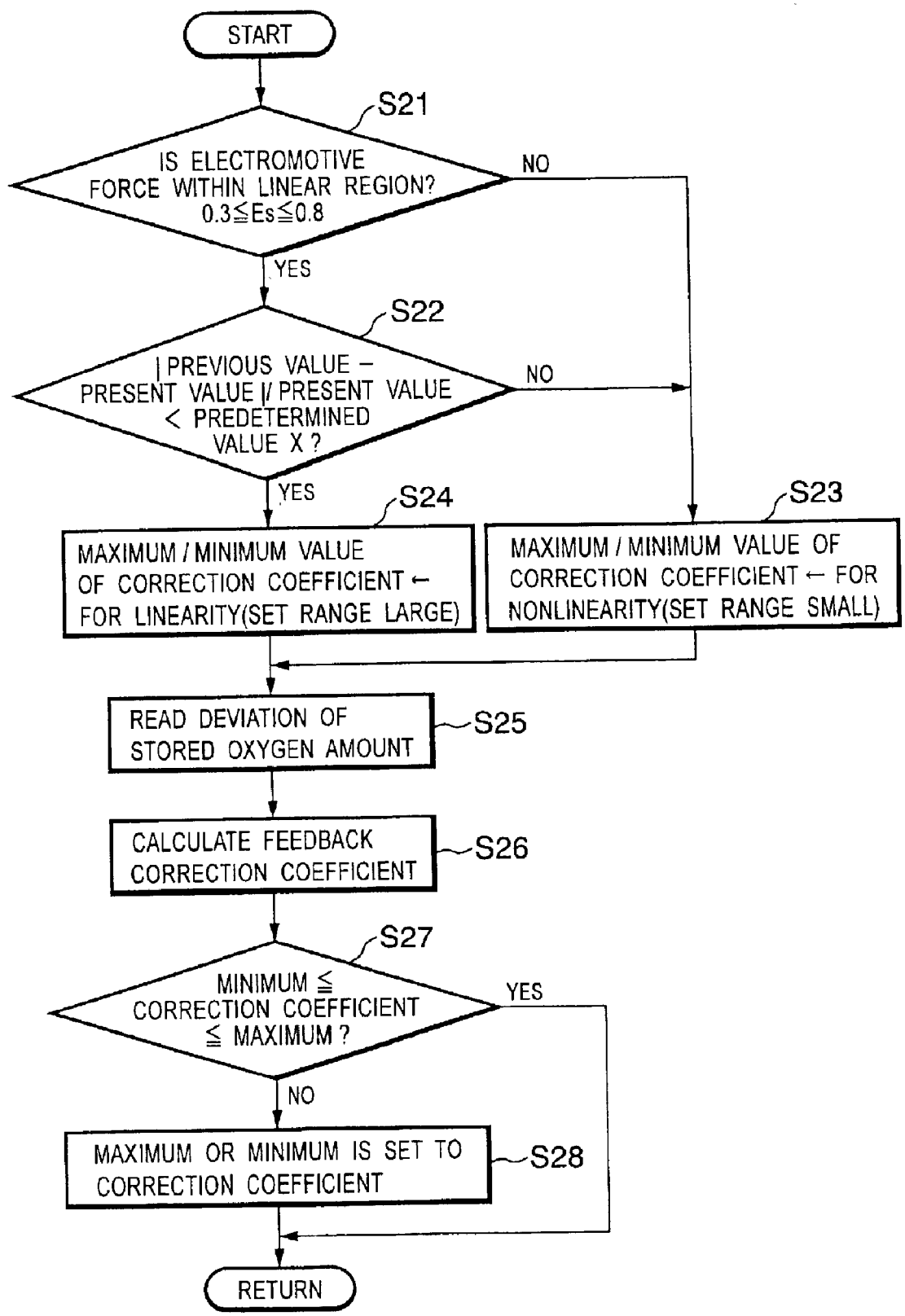
FIG. 6 is a flowchart showing a third embodiment of feedback correction coefficient calculation.

A flowchart of FIG. 6 shows an embodiment in which a limit value of the air-fuel ratio feedback correction coefficient is switched between within the linear region and outside the linear region.

In the flowchart of FIG. 6, at steps S21 and S22, similar to steps S1 and S2, it is judged whether or not the electromotive force Es of oxygen sensor 27 is within the linear region, and if within the linear region, it is also judged whether or not the electromotive force Es is stabled within the linear region.

If the electromotive force Es of oxygen sensor 27 is outside the linear region and if there is a high possibility that the electromotive force will be displaced to the outside of the linear region although it is currently within the linear region, control proceeds to step S23.

At step S23, values maxA and minA adapted to the time when the electromotive force is outside the linear region are set to a maximum value max and a minimum value min of the air-fuel ratio feedback correction coefficient.

On the other hand, if the electromotive force Es of oxygen sensor 27 is within the linear region and also stabled within it, control proceeds to step S24.

At step S24, values maxB and minB adapted to the time when the electromotive force is within the linear region are set to the maximum value max and the minimum value min of the air-fuel ratio feedback correction coefficient.

Here, maxB>maxA, minB<minA.

Accordingly, if the electromotive force is outside the linear region, a setting range of the air-fuel ratio feedback correction coefficient is limited within a narrower range in the vicinity of a reference value (=1.0).

At step S25, the error of the stored oxygen amount is read in.

At step S26, the air-fuel ratio feedback correction coefficient is calculated based on the error of the stored oxygen amount.

At step S27, it is judged whether or not the air-fuel ratio feedback correction coefficient calculated at step S26 is within the setting range between the maximum value max and the minimum value min set at step S23 or at step S24.

Then, if the air-fuel ratio feedback correction coefficient is deviated from the setting range, control proceeds to step S28.

At step S28, the maximum value max is set to the air-fuel ratio feedback correction coefficient if the air-fuel ratio feedback correction coefficient exceeds the maximum value max, while the minimum value min is set to the air-fuel ratio feedback coefficient if lower than the minimum value min.

Here, if the electromotive force Es of oxygen sensor 27 is outside the linear region, since the air-fuel ratio feedback correction coefficient is limited within the narrow range in the vicinity of the reference value, it can be avoided that the air-fuel ratio feedback correction coefficient is set to a value greatly apart from the reference value, thereby enabling to suppress the influence of the air-fuel ratio detection error.

In the above embodiment, the constitution has been such that the fuel injection quantity is feedback controlled so that the stored oxygen amount estimated based on the air-fuel ratio detected by oxygen sensor 27 coincides with a target. However, the constitution may be such that the fuel injection quantity is feedback controlled so that the air-fuel ratio detected by oxygen sensor 27 coincides with a target air-fuel ratio.

Figure 7:
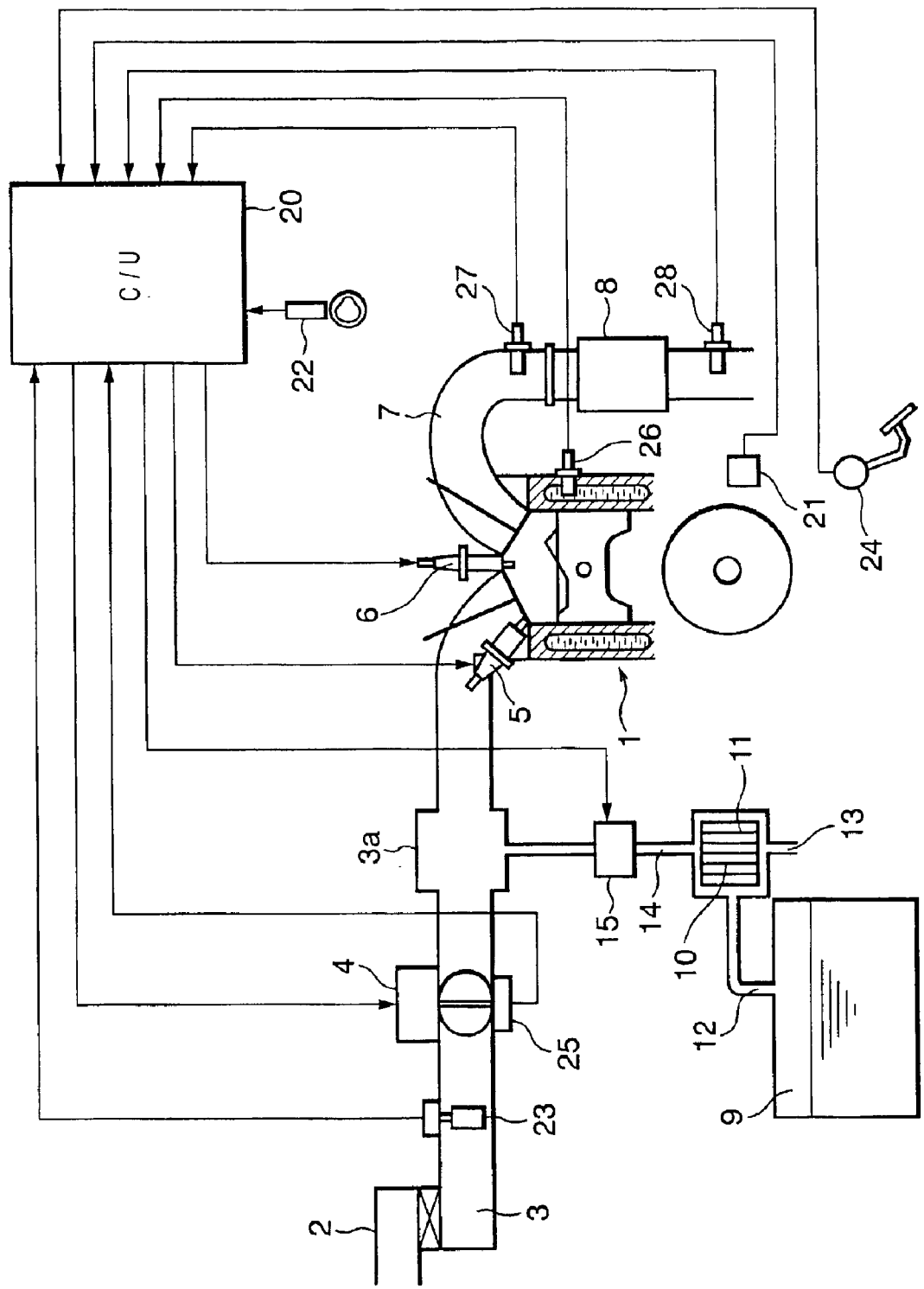
FIG. 7 is a diagram showing another system structure of the engine

FIG. 7 is a diagram showing an entire constitution of an engine in embodiments for controlling a heater of oxygen sensor 27.

The engine shown in FIG. 7 is similar to that shown in FIG. 1, except that a fuel vapor treating apparatus is additionally provided, and an oxygen sensor 28 is disposed on the downstream side of catalyst 8.

Accordingly, the same components are denoted by the same reference numerals and the description thereof is omitted.

The fuel vapor treating apparatus is for combusting to treat fuel vapor generated in a fuel tank 9.

A canister 10 is a sealed container filled with an adsorbent 11 such as active carbon, and is connected with a fuel vapor inlet pipe 12 extending from fuel tank 9.

Fuel vapor generated in fuel tank 9 is introduced to canister 10 passing through fuel vapor inlet pipe 12, to be collectively adsorbed by canister 10.

Further, canister 10 is formed with a new air inlet opening 13, and also a purge piping 14 is introduced from canister 10.

Purge piping 14 is communicated with an intake air collector 3a of engine 1.

Purge piping 14 is disposed with a purge control valve 15, an opening of which is controlled by a control signal from control unit 20.

In the above constitution, when purge control valve 15 is controlled to open, an intake negative pressure of engine 1 acts on canister 10.

As a result, fuel vapor adsorbed to adsorbent 11 of canister 10 is purged by air introduced from new air inlet opening 13, and purge air passes through purge piping 14 to flow into intake air collector 3a, and thereafter is combusted to be treated within the combustion chamber of engine 1.

Oxygen sensor 28 is, similar to oxygen sensor 27, an oxygen sensor of oxygen concentration cell type generating an electromotive force according to a ratio between oxygen concentration in engine exhaust air outside the zirconia tube and oxygen concentration in the atmosphere inside the zirconia tube.

Oxygen sensor 28 is the one exhibiting a stoichiometric characteristic in which an output thereof is abruptly changed on reaching the stoichiometric air-fuel ratio.

On the contrary, oxygen sensor 27, as described above, compositions of element thereof or manufacturing method thereof are adjusted so that the output thereof exhibits linearity to the air-fuel ratio within the predetermined air-fuel ratio range (the electromotive force range of from 0.3 to 0.8 mV) inclusive of the stoichiometric air-fuel ratio.

Figure 8:
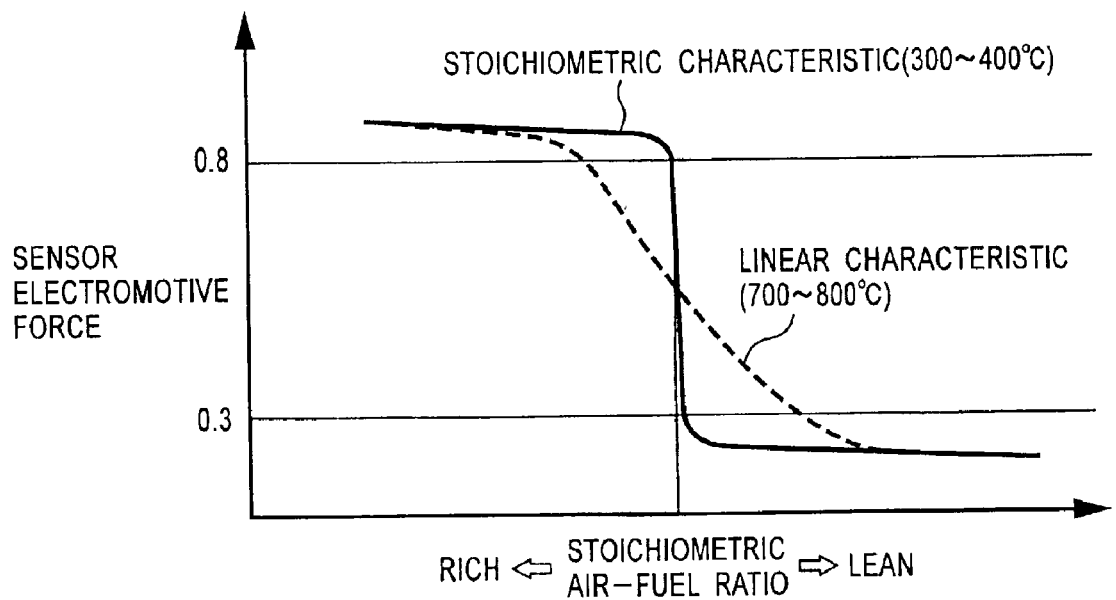
FIG. 8 is a graph showing a change in output characteristic of the oxygen sensor due to an element temperature.

However, as shown in FIG. 8, oxygen sensor 27 exhibits the linearity, when an element temperature is at about 700 to 800° C. (a second temperature region), but exhibits the stoichiometric characteristic in which the output thereof is abruptly changed on reaching the stoichiometric air-fuel ratio, when the element temperature is lower than the above temperature, about 300 to 400° C. (a first temperature region).

Figure 9:
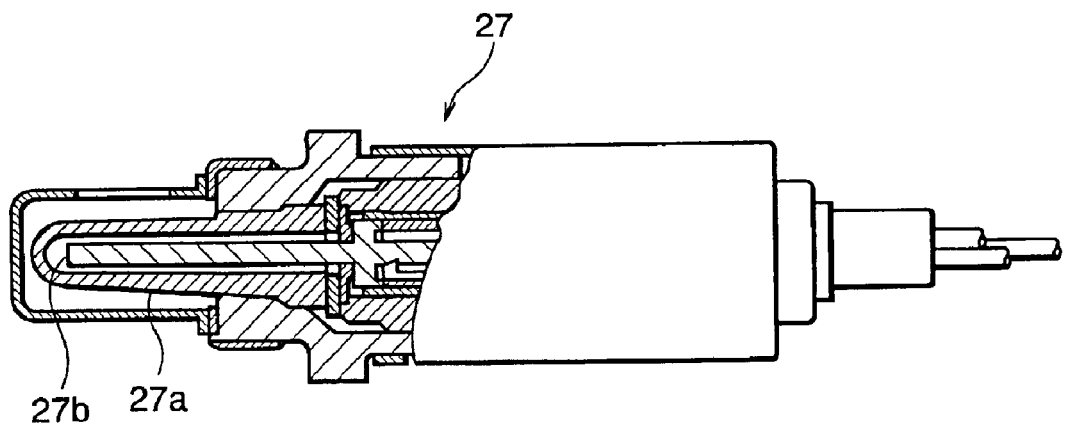
FIG. 9 is a partial section view showing a structure of the oxygen sensor.

FIG. 9 shows a structure of oxygen sensor 27, in which a rod type ceramic heater 27b is inserted into a hollow portion of a zirconia tube 27a of oxygen sensor 27.

The power supply to ceramic heater 27b is controlled by control unit 20.

Note, oxygen sensors 27 and 28 are not limited to those of zirconia tube type, but may be of a plate type. Further, those sensors may be the one using an element other than zirconia.

Control unit 20 controls the power supply to ceramic heater 27b and also detects the air-fuel ratio based on the electromotive force Es of oxygen sensor 27, to perform the air-fuel ratio feedback control based on the detection result.

Figure 10:
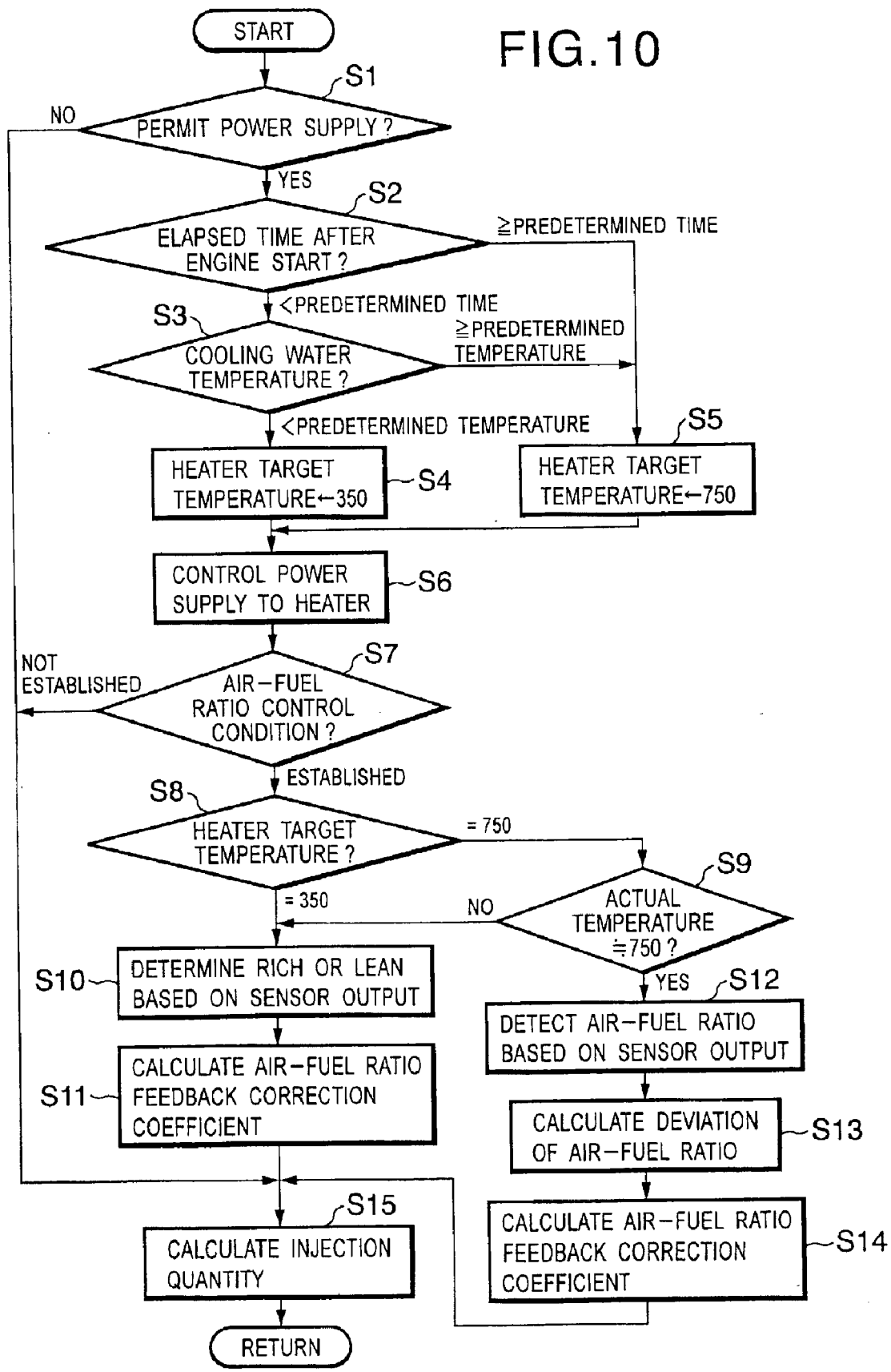
FIG. 10 is a flowchart showing a first embodiment of a heater temperature control.

A flowchart of FIG. 10 shows the detail of the air-fuel ratio feedback control.

At step S1, it is judged whether or not a permission condition of the power supply to ceramic heater 27b is established.

The permission condition includes that a disconnection or a short-circuited of a power supply circuit of ceramic heater 27b does not occur.

If the permission condition is established, control proceeds to step S2.

At step S2, it is judged whether or not an elapsed time t from the start of engine 1 becomes a predetermined time t1 (for example, 15 seconds) or longer.

If the elapsed time t is shorter than the predetermined time t1, control proceeds to step S3.

At step S3, it is judged whether or not a cooling water temperature Tw at that time is a predetermined temperature Tw1 or above.

Note, the cooling water temperature Tw used here is for representing an exhaust pipe temperature in the vicinity of oxygen sensor 27.

Accordingly, a temperature sensor may be disposed for detecting the exhaust pipe temperature in the vicinity of oxygen sensor 27, to judge whether or not the exhaust pipe temperature is a predetermined temperature (for example, 65° C.) or above.

Further, the exhaust pipe temperature may be estimated from the elapsed time from engine start, an intake air amount (exhaust gas flow amount), a water temperature at engine start and the like.

If it is judged that the elapsed time t is shorter than the predetermined time t1 and also the cooling water temperature Tw is lower than the predetermined temperature Tw1 (the exhaust pipe temperature is lower than the predetermined temperature), control proceeds to step S4.

At step S4, a target temperature in the power supply control to ceramic heater 27b is set to 350° C. 350° C. is a center value of a temperature range where oxygen sensor 27 exhibits the stoichiometric characteristic.

On the other hand, if the elapsed time t is the predetermined time t1 or longer, or if the elapsed time t is shorter than the predetermined time t1 but the cooling water temperature Tw is the predetermined temperature Tw1 or above, control proceeds to step S5.

At step S5, the target temperature in the power supply control to ceramic heater 27b is set to 750° C. 750° C. is a center value of a temperature range where oxygen sensor 27 exhibits the linearity to the air-fuel ratio.

At step S6, the power supply to ceramic heater 27b is controlled in accordance with the target temperature set at step S4 or at step S5.

The power supply control is performed by a duty control of a switching element that switches the power supply.

In the duty control, a duty ratio may be feedback controlled in accordance with the target temperature, or an internal resistance indicating the element temperature of oxygen sensor 27 may be detected to perform the feedback control so that the detected internal resistance reaches an internal resistance equivalent to the target temperature.

If the elapsed time t is shorter than the predetermine time t1, and also the cooling water temperature Tw is lower than the predetermined temperature Tw1, it is estimated that a water adhered to the element of oxygen sensor or the peripheral exhaust pipe during engine stall remains as it is.

Then, at this time, if the target temperature of heater is set to a high temperature at which oxygen sensor 27 exhibits the linearity to the air-fuel ratio, there is a possibility that element cracking occurs due to thermal shock.

Therefore, if the elapsed time t is shorter than the predetermine time t1, and also the cooling water temperature Tw is lower than the predetermined temperature Tw1, the target temperature is set to be low, to avoid the occurrence of thermal shock.

Incidentally, the process of step S3 may be omitted to judge the water adhered state based on only the elapsed time t from engine start.

At step S7, it is judged whether or not an air-fuel ratio feedback control condition is established.

The air-fuel ratio feedback control condition includes that an engine load and an engine rotation speed are within predetermined regions and it is not a deceleration time.

If the air-fuel ratio feedback control condition is established, control proceeds to step S8.

At step S8, it is judged which of 350° C. or 750° C. the target temperature in the power supply control to ceramic heater 27b is set to.

If the target temperature is 350° C. (the first temperature region), oxygen sensor 27 exhibits the stoichiometric characteristic.

Therefore, control proceeds to step S10, wherein the electromotive force Es of oxygen sensor 27 and a value equivalent to stoichiometric air-fuel ratio (for example, 500 mV) are compared with each other, to judge whether an actual air-fuel ratio is richer or leaner than the stoichiometric air-fuel ratio.

At next step S11, an air-fuel ratio feedback correction coefficient a for correcting a basic fuel injection quantity Tp is set based on the rich/lean judging result of the actual air-fuel ratio to the stoichiometric air-fuel ratio.

At step S15, a final fuel injection quantity Ti is calculated based on the air-fuel ratio feedback correction coefficient $\alpha$.

On the other hand, if it is judged at step S8 that the target temperature in the power supply control to ceramic heater 27b is 750° C. (the second temperature region), control proceeds to step S9.

At step S9, it is judged whether or not the element temperature of oxygen sensor 27 becomes around 750° C.

The judgment at step S9 can be performed by an estimation based on an elapsed time after the target temperature becomes 750° C. or the temperature detection based on the detection of internal resistance.

The reason why it is judged whether or not the element temperature becomes 750° C. when the target temperature is 750° C. as mentioned above is that there is a large delay in the sensor element temperature for reaching around the target temperature since the target temperature is high.

If it is judged at step S9 that the element temperature of oxygen sensor 27 does not reach around 750° C., control proceeds to step S10, similarly to the case where the target temperature is 350° C.

Then, it is judged whether the actual air-fuel ratio is richer or leaner than the stoichiometric air-fuel ratio on the condition that oxygen sensor 27 exhibits the stoichiometric air-fuel ratio.

If it is judged at step S9 that the element temperature of oxygen sensor 27 actually reaches around 750° C., control proceeds to step S12.

If the element temperature of oxygen sensor 27 is around 750° C., since the electromotive force Es exhibits the linearity to the air-fuel ratio, then at step S12, the electromotive force Es of oxygen sensor 27 is converted into an air-fuel ratio to detect the air-fuel ratio in a wide range.

Note, even if the element temperature of oxygen sensor 27 is around 750° C., a range where the electromotive force Es exhibits the linearity to the air-fuel ratio is limited to the predetermined air-fuel ratio range inclusive of the stoichiometric air-fuel ratio (the electromotive force range of from 0.3 to 0.8 mV). Consequently, at the outside of the predetermined air-fuel ratio range, the detection accuracy of air-fuel ratio is significantly reduced.

Therefore, when the electromotive force Es is deviated from an output range corresponding to the predetermined air-fuel ratio range, the detection result of air-fuel ratio may be fixed to a minimum air-fuel ratio (a rich side boundary air-fuel ratio) or a maximum air-fuel ratio (a lean side boundary air-fuel ratio) defining the predetermined air-fuel ratio, or the rich/lean judgment of the actual air-fuel ratio to the stoichiometric air-fuel ratio may be performed.

At step S13, a deviation between the air-fuel ratio detected at step S12 and the target air-fuel ratio (stoichiometric air-fuel ratio) is calculated.

At step S14, the air-fuel ratio feedback correction coefficient a is calculated based on the air-fuel ratio deviation.

According to the above embodiment, when the water is adhered to oxygen sensor 27 immediately after engine start and a heating permissive temperature is low, oxygen sensor 27 is not heated to a high temperature, thereby avoiding element cracking due to thermal shock.

Further, even if it is impossible to heat the element to a high temperature at which the electromotive force Es of oxygen sensor 27 exhibits the linearity to the air-fuel ratio since there is a possibility of element cracking, the element is heated to a temperature at which oxygen sensor 27 exhibits the stoichiometric characteristic.

Accordingly, the air-fuel ratio feedback control can be performed based on the rich/lean judgment of the air-fuel ratio in early timing after start of engine 1.

Further, during a period until the element temperature actually reaches 750° C. after the target temperature is switched to 750° C. after the condition in which thermal shock does not occur is achieved, the air-fuel ratio can be feedback controlled based on the rich/lean judgment of the air-fuel ratio, and also the air-fuel ratio can be feedback controlled in the early timing after engine start, to improve the exhaust emission immediately after engine start.

Moreover, after the element temperature actually reaches 750° C., by detecting the air-fuel ratio in a wide range, it is possible to perform the air-fuel ratio feedback control excellent in response characteristic and stability to the target air-fuel ratio.

Incidentally, in the embodiment shown in the flowchart of FIG. 10, the constitution has been such that if the condition in which element cracking does not occur is achieved, the heater target temperature is fixed to 750° C.

However, the constitution may be such that even after the condition in which element cracking does not occur is achieved, the heater target temperature is set to 750° C. only when a wide range air-fuel ratio detection is required in response to a request by the air-fuel ratio control. Such a constitution will be described in accordance with a flowchart of FIG. 11.

Figure 11:
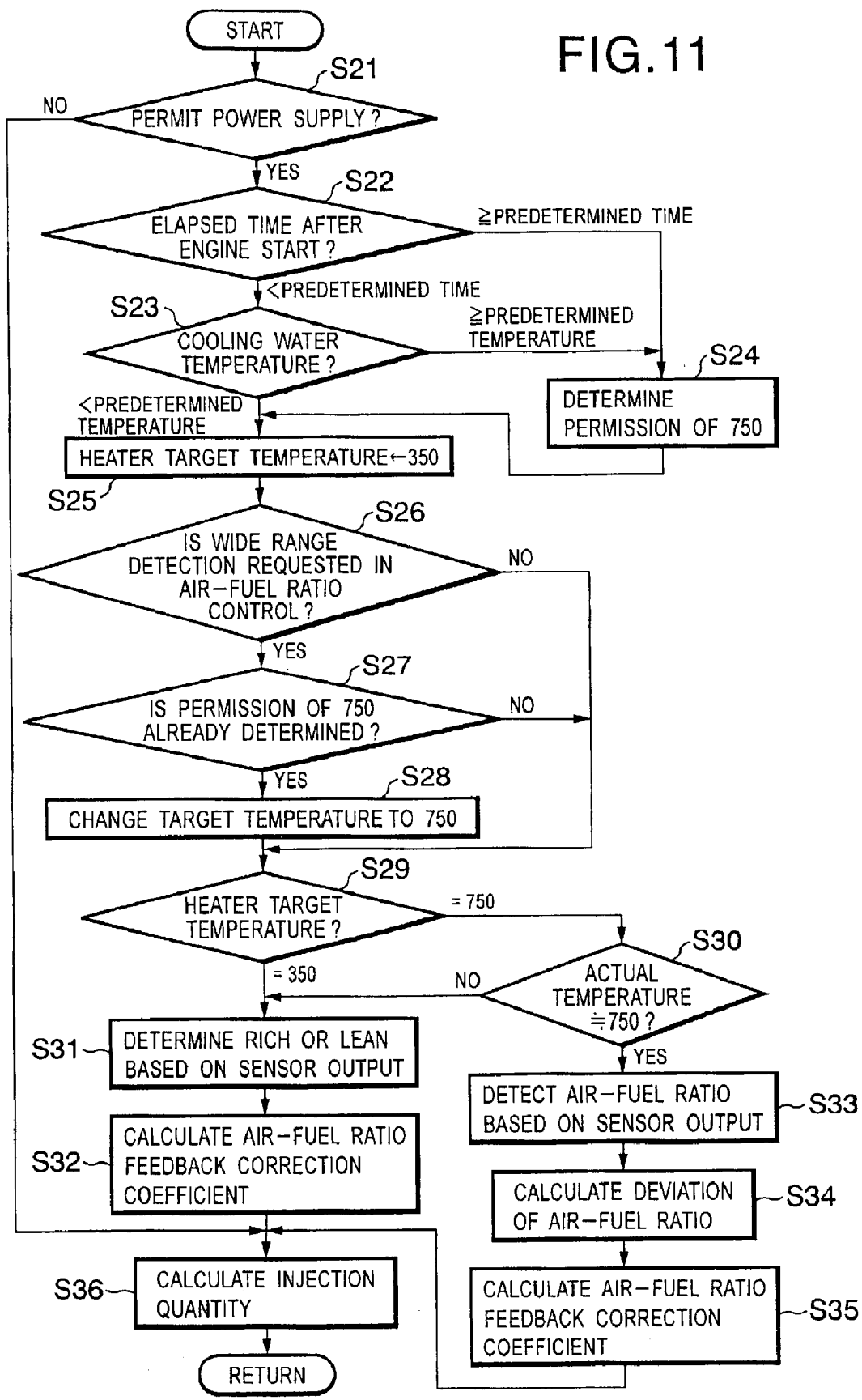
FIG. 11 is a flowchart showing a second embodiment of the heater temperature control.

In the flowchart of FIG. 11, if it is judged at step S21 that the power supply is permitted, and further, if it is judged at step S22 or at step 23 that the condition of the elapsed time after engine start or the water temperature becomes the condition in which element cracking does not occur, control proceeds to step S24.

At step S24, it is judged that the condition in which the heater target temperature can be switched to 750° C. is established.

At step S25, 350° C. being a basic temperature is set to the heater target temperature.

At step S26, it is judged whether or not the air-fuel ratio control requests the wide range air-fuel ratio detection.

The condition in which the wide range air-fuel ratio detection is requested, is a condition in which, for example, the target air-fuel ratio in the air-fuel ratio feedback control is set to a lean or rich air-fuel ratio.

If it is judged at step S26 that the wide range air-fuel ratio detection is not requested, the heater target temperature is maintained at 350° C. as it is, then control proceeds to step S29.

On the other hand, if it is judged at step S26 that the wide range air-fuel ratio detection is requested, then control proceeds to step S27.

At step S27, it is judged whether or not it is judged at step S24 that the target temperature can be switched to 750° C.

Even in a condition in which the wide range air-fuel ratio detection is requested, since it is impossible to switch the target temperature to 750° C. under the condition of the possibility of element cracking, the heater target temperature is maintained at 350° C. as it is, and control proceeds to step S29.

If it is judged that the target temperature can be switched to 750° C., control proceeds to step S28, wherein the heater temperature is switched to 750° C.

At subsequent steps S29 to S36, processes are executed similarly to steps S8 to S15 in the flowchart of FIG. 10.

That is, if the target temperature is 750° C., and the actual element temperature reaches 750° C., the air-fuel ratio is detected in a wide range based on the sensor output so that the air-fuel ratio feedback control with the air-fuel ratio other than the stoichiometric air-fuel ratio as the target air-fuel ratio can be performed.

On the contrary, if the target temperature is 350° C., and if the actual temperature does not reach 750° C. although the target temperature is 750° C., the rich/lean judgment of the air-fuel ratio to the stoichiometric air-fuel ratio is executed, to perform the air-fuel ratio feedback control with the stoichiometric air-fuel ratio as the target air-fuel ratio.

Figure 12:
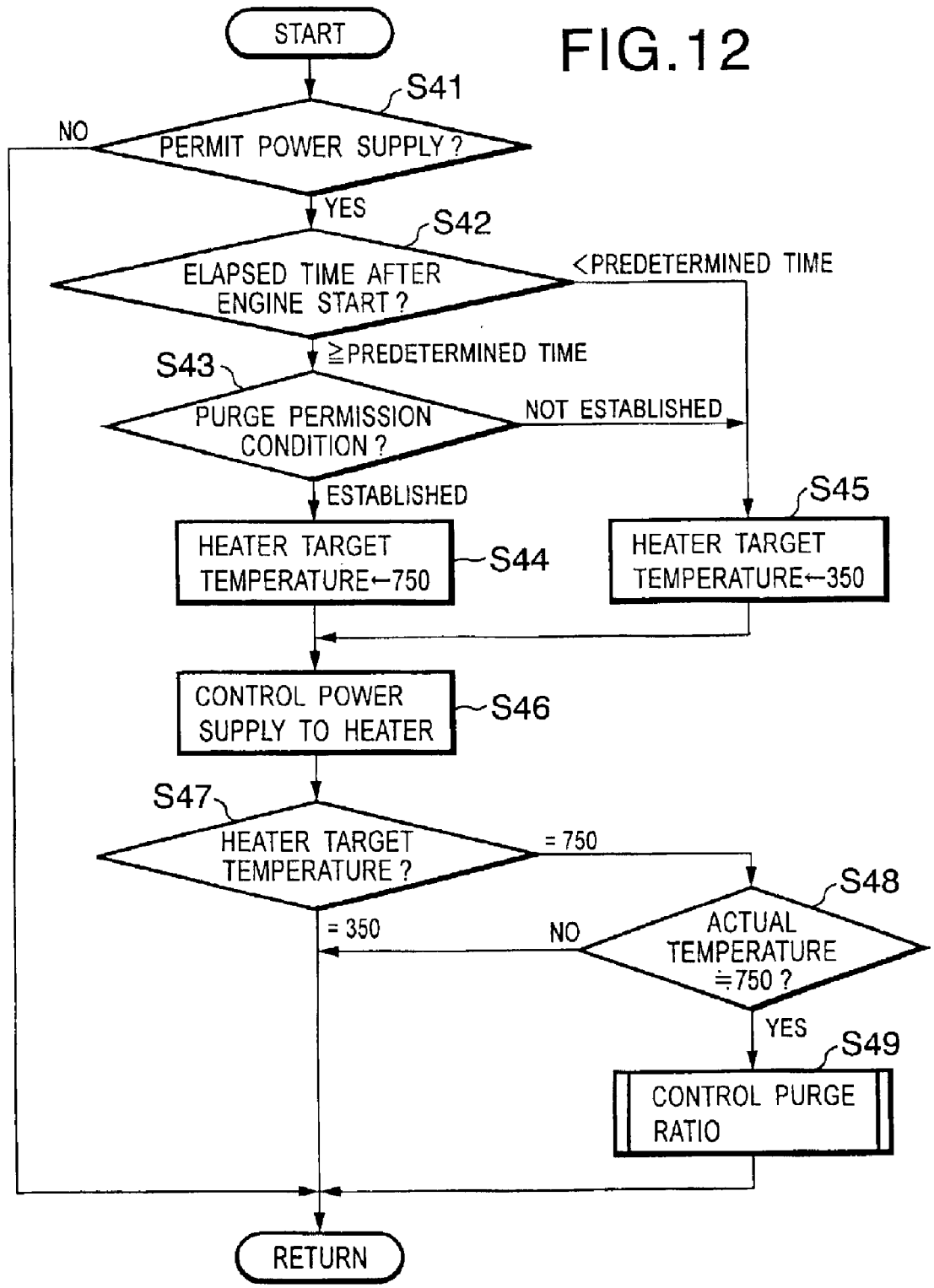
FIG. 12 is a flowchart showing a third embodiment of the heater temperature control.

FIG. 12 shows an embodiment in which the heater target temperature is switched in correlative to the canister purge control.

In a flowchart of FIG. 12, at step S41, it is judged whether or not the permission condition of the power supply to ceramic heater 27b is established.

If the permission condition is established, control proceeds to step S42 wherein it is judged whether or not the elapsed time t from the start of engine 1 becomes the predetermined time t1 or longer.

Then, if the elapsed time t is equal to or longer than the predetermined time t1, control proceeds to step S43.

At step S43, it is judged whether or not a canister purge executing condition for purging fuel vapor collectively adsorbed to canister 10 to supply the purged fuel vapor to engine 1, is established.

If the canister purge executing condition is established, the air-fuel ratio is detected in a wide range by oxygen sensor 27 to estimate purge air concentration, and a purge ratio is controlled based on the estimated purge air concentration.

Therefore, if it is judged at step S43 that the canister purge executing condition is established, control proceeds to step S44 wherein 750° C. is set to the target temperature in the power supply control to ceramic heater 27b.

On the other hand, if the elapsed time t from engine start is shorter than the predetermined time t1, or if the canister purge executing condition is not established, control proceeds to step S45 wherein 350° C. is set to the heater target temperature.

That is, at a normal time when the purge control is not performed even if the elapsed time from engine start is the predetermined time t1 or longer, the heater target temperature is set to 350° C.

At this time, since oxygen sensor 27 exhibits the stoichiometric characteristic, in the air-fuel ratio feedback control using oxygen sensor 27, the setting of air-fuel ratio feedback correction coefficient is performed even after engine warm-up, based on the rich/lean judgment result.

At step S46, the power supply to ceramic heater 27b is controlled in accordance with the target temperature set at step S44 or at step S45.

At step S47, it is judged which of 350° C. or 750° C. the target temperature in the power supply control to ceramic heater 27b is set to.

If it is judged at step S47 that the target temperature in the power supply control to ceramic heater 27b is 750° C. (the second temperature region), control proceeds to step S48.

At step S48, it is judged whether or not the element temperature of oxygen sensor 27 actually reaches around 750° C., and if the element temperature reaches around 750° C., control proceeds to step S49 to perform the purge ratio control.

Figure 13:
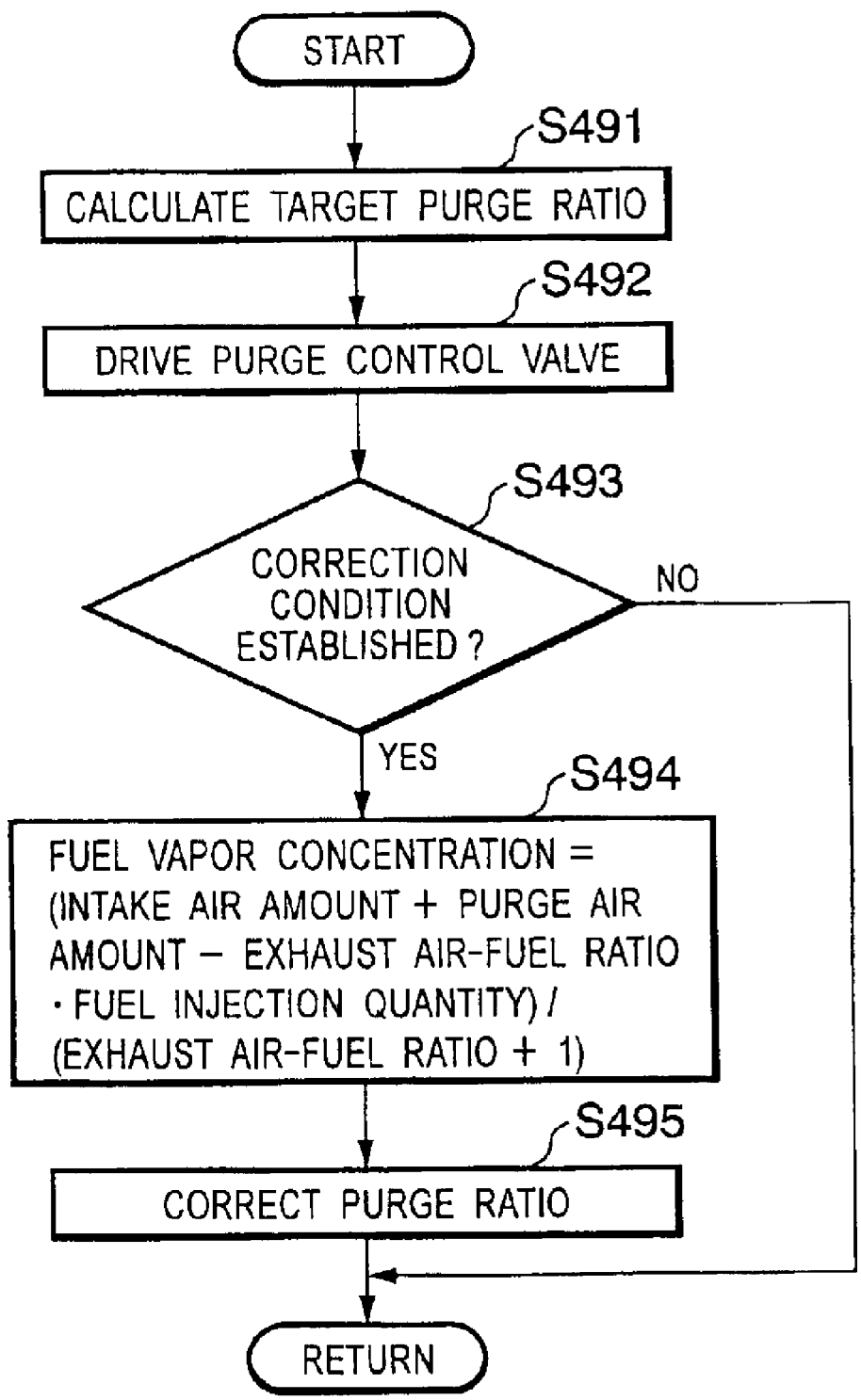
FIG. 13 is a flowchart showing a purge ratio correction control.

The detail of purge ratio control in step S49 is shown in a flowchart of FIG. 13.

At step S491, a target purge ratio is calculated based on operating conditions of engine 1.

At step S492, a control signal according to the target purge ratio is output to purge control valve 15.

At step S493, it is judged whether or not a correction control permission condition of purge ratio is established.

The correction control permission condition includes that air flow meter 23 is normal, a predetermined time has elapsed from the target purge ratio is changed, and the like.

If it is judged at step S493 that the correction control permission condition of purge ratio is established, control proceeds to step S494 wherein the purge air concentration (fuel concentration in purge air) is calculated.

The calculation of fuel vapor concentration at step S494 is simply represented by the following equation.

Fuel vapor concentration=(intake air amount+purge air amount−air-fuel ratio×fuel injection quantity)/(air-fuel ratio+1)

In the above equation, the intake air amount is a detected value of air flow meter 23, the purge air amount is a value estimated from the intake negative pressure of engine 1 and a control signal (opening area) of purge control valve 15, the air-fuel ratio is a value obtained based on the electromotive force Es of oxygen sensor 27, and the fuel injection quantity is an injected fuel quantity from fuel injection valve 5.

Note, the intake negative pressure of engine 1 may be directly detected by disposing a negative pressure sensor or may be estimated from the engine rotation speed and the throttle opening.

Here, it is assumed that a purge air amount Pe is composed of an air amount Qp and a fuel gas amount Fe, a value obtained by subtracting the fuel gas amount Fe from the purge air amount Pe is the air amount Qp.

$Qp=Pe-Fe$

Then, a sum of the air amount Qp and an air amount Qm detected by air flow meter 23 is sucked into engine 1.

On the other hand, the fuel quantity supplied to engine 1 is a sum of an injected fuel quantity Ti from fuel injection valve 5 and the fuel gas amount Fe.

Accordingly, if the air-fuel ratio at that time is A/F, the following equation is established, $A/F=\{(Pe-Fe)+Qm\}/(Fe+Ti)$.

Then, this equation is transformed to an equation for obtaining the fuel gas amount Fe, $Fe=(Pe+Qm-A/F \cdot Ti)/(A/F+1)$, to lead an equation for obtaining the purge air concentration.

However, the purge air amount Pe and the air amount Qm are obtained as flow amounts (litter/min), while the injected fuel quantity Ti is a fuel quantity per one cycle in each cylinder. Therefore, the injected fuel quantity Ti is required to be converted to a fuel flow amount.

Therefore, the injected fuel quantity Ti is multiplied, for example, by a conversion coefficient K1 set according to an engine rotation speed Ne, to be converted to the fuel flow quantity.

Further, in the constitution in which the purge air amount is estimated from the intake negative pressure and the control signal of purge control valve 15, a control signal DUTY of purge control valve 15 may be multiplied by a coefficient K2 according to the intake negative pressure, to calculate a value equivalent to the purge air amount. In the constitution using the coefficients K1 and K2, the following equation is established.

Purge air concentration=$(Qm+K2 \cdot DUTY - A/F \cdot Ti \cdot K1)/(A/F+1)$.

At step S495, the purge ratio is corrected to be smaller as actual purge air concentration is higher than reference purge air concentration, while the purge ratio is corrected to be larger as the actual purge air concentration is lower than the reference purge air concentration.

In the embodiment shown in FIG. 12, the constitution has been such that the heater target temperature is maintained at 750° C. during the purge permission condition is established.

However, the estimation of purge air concentration in which the wide range air-fuel ratio detection is requested, is not necessarily performed repeatedly in short periods.

Therefore, the constitution may be such that during the purge permission condition is established, the heater target temperature is periodically switched to 750° C., to update the purge air concentration in each period.

Figure 14:
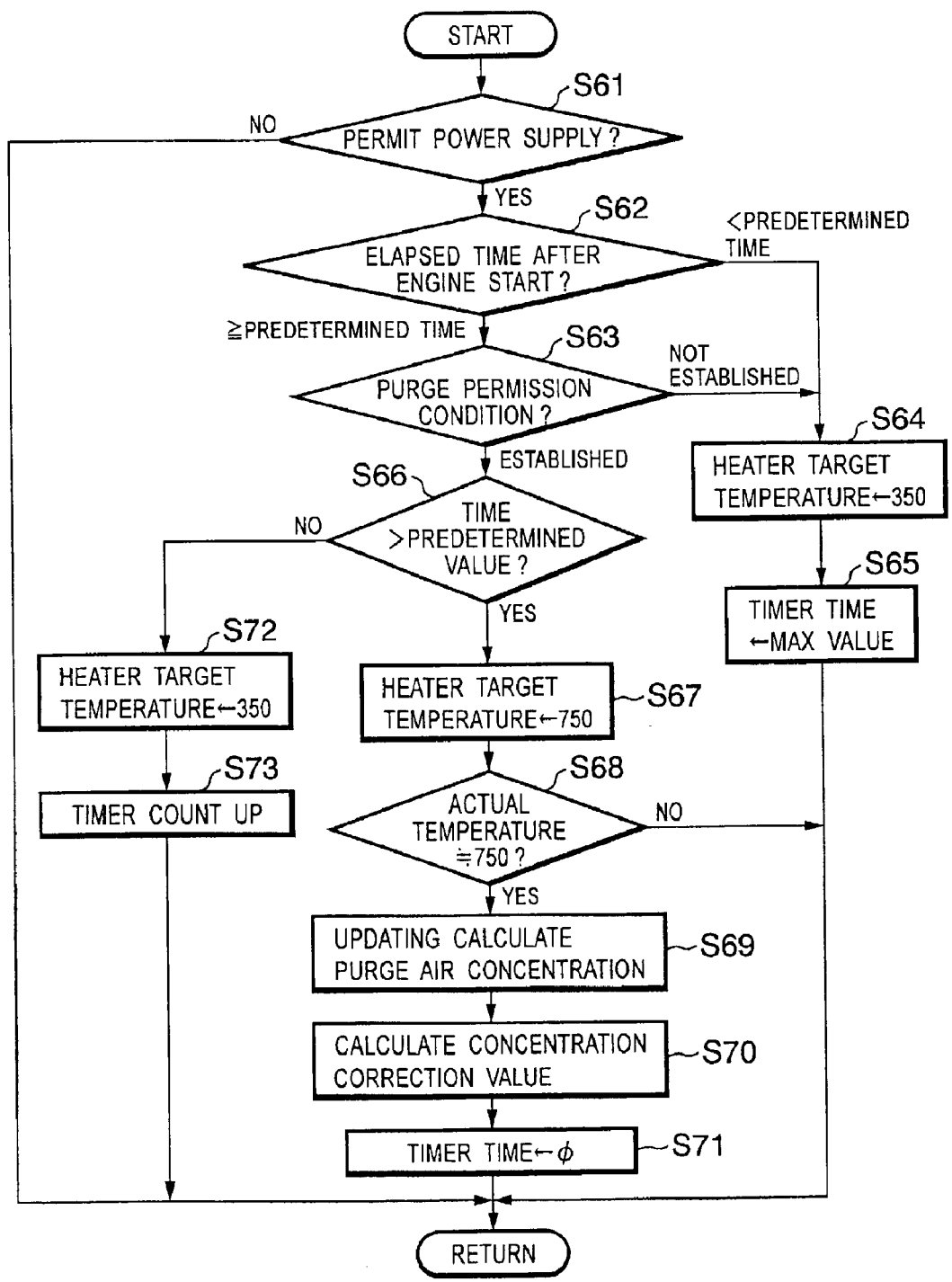
FIG. 14 is a flowchart showing a fourth embodiment of the heater temperature control.

A flowchart of FIG. 14 shows an embodiment in which the heater target temperature is periodically switched to 750° C. during the purge permission condition is established, as described above.

In the flowchart of FIG. 14, at step S61, it is judged whether or not the power supply to the heater is permitted, and if the power supply is not permitted, the present control routine is terminated.

If the power supply is permitted, it is judged at step S62 whether or not the elapsed time from engine start is the predetermined time or longer, and if the elapsed time is the predetermined time or longer, control proceeds to step S63 wherein it is judged whether or not the purge permission condition is established.

If the elapsed time from engine start is shorter than the predetermined time, and if the purge permission condition is not established, control proceeds to step S64 wherein the heater target temperature is set to 350° C.

Further, at next step S65, a maximum value MAX is set to a timer TIME.

If the elapsed time from engine start is the predetermined time or longer, and also the purge permission condition is established, control proceeds to step S66 wherein it is judged whether or not the timer TIME exceeds a predetermined value.

In the case where control proceeds to step S66 for the first time, since the timer TIME=MAX, it is judged that the timer TIME exceeds the predetermined value, control proceeds to step S67.

At step S67, the heater target temperature is switched to 750° C.

Then, at step S68, it is judged whether or not the element temperature actually reaches 750° C., and if the actual temperature does not reach 750° C., the present control routine is terminated while maintaining heater target temperature=750° C. and timer TIME=MAX.

If the actual temperature reaches 750° C., control proceeds to step S69 wherein the air-fuel ratio is detected in a wide range based on the electromotive force Es of oxygen sensor 27, to calculate the purge air concentration as shown in step S494 in the flowchart of FIG. 13.

At step S70, a purge ratio correction value according to the purge air concentration obtained at step S69 is set.

The purge ratio correction value is used for correcting a target purge ratio previously set for each operating condition.

At step S71, the timer TIME is reset to zero.

By resetting the timer TIME to zero at step S71, at next step S66, it is judged that the timer TIME is the predetermined value or less, then control proceeds to step S72.

At step S72, the heater target temperature is returned to 350° C., and at step S73, the timer TIME is counted up.

Accordingly, when the heater target temperature is switched to 750° C. at an initial time when the purge permission condition is established, and the element temperature actually reaches 750° C., if the purge air concentration and the purge ratio correction value are calculated, the heater target temperature is maintained at 350° C. during a period until the timer TIME is counted up from zero to the predetermined value, and a calculation result at an initial time is used as it is for the purge ratio correction value.

If the timer TIME is counted up from zero to the predetermined value, the heater target temperature is again switched to 750° C., and the purge air concentration and the purge ratio correction value are calculated to be updated.

Timing of switching the heater target temperature to 750° C. and calculating to update the purge air concentration and the purge ratio correction value may be set to each fixed time measured by the timer TIME or each time when a change in purge air concentration is expected.

Figure 15:
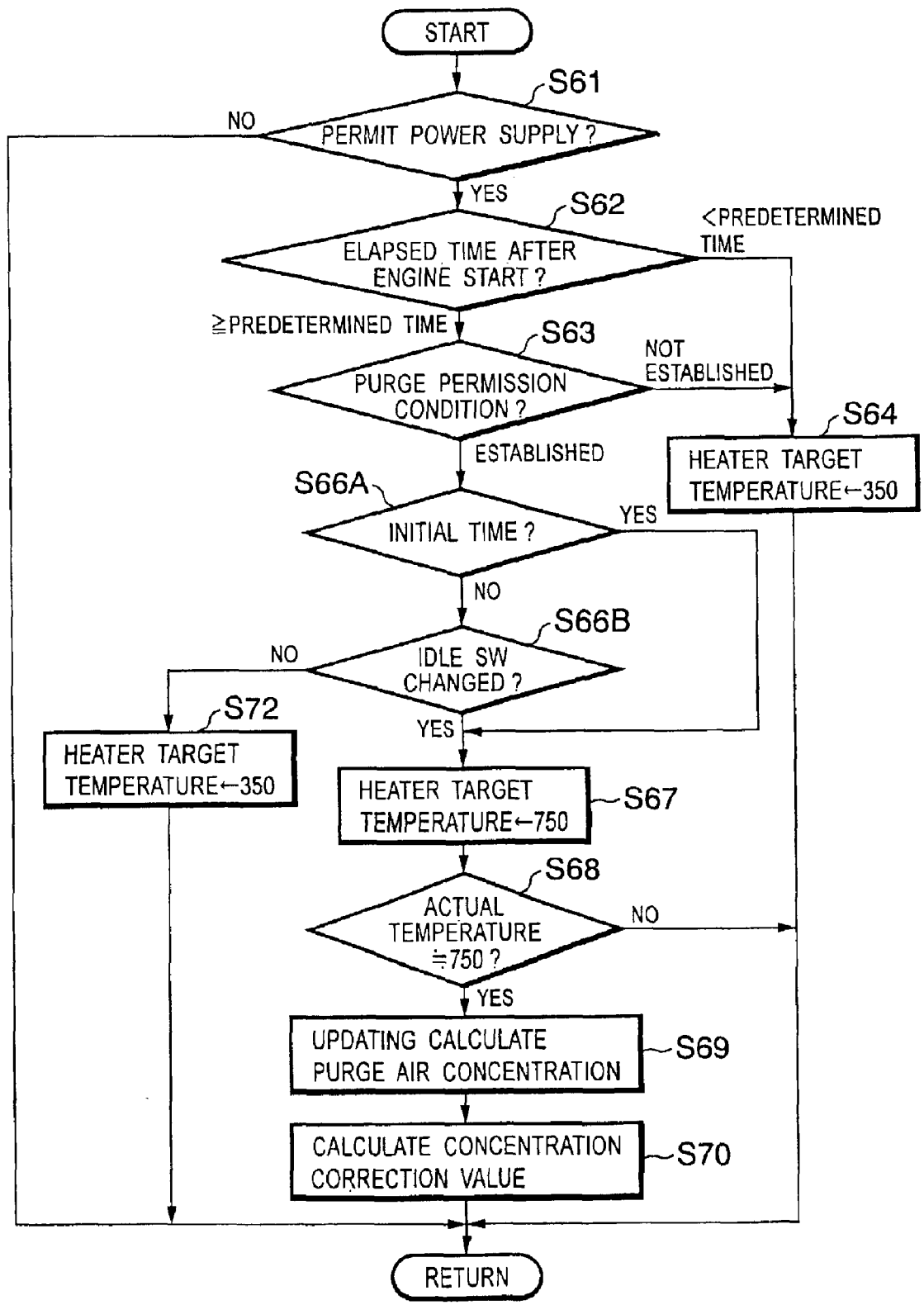
FIG. 15 is a flowchart showing a fifth embodiment of the heater temperature control.

A flowchart of FIG. 15 shows an embodiment in which the timing of switching the heater target temperature to 750° C. and calculating to update the purge air concentration and the purge ratio correction value is set to each time when an idle switch is turned ON or OFF.

The idle switch is the one that is turned ON when the throttle valve is fully closed and is turned OFF when the throttle valve is opened.

That is, in this embodiment, timing in which operating conditions are changed and a vapor generating amount is increased or decreased is set to timing in which an idle operating condition is switched to a non-idle operating condition or the non-idle operating condition is switched to the idle operating condition, to update the purge air concentration with the heater temperature as 750° C. at each switching.

In this embodiment shown in the flowchart of FIG. 15, at step S66A, it is judged whether or not it is the initial time the purge permission condition is established, and if it is the initial time, control proceeds from step S66A to step S67 wherein the heater target temperature is switched to 750° C. to calculate the purge air concentration and the purge ratio correction value.

Thereafter, the heater target temperature is maintained at 350° C. until it is judged at step S66B that the idle switch is turned ON or OFF.

Then, it is judged at step S66B that the idle switch is turned ON or OFF, control proceeds to step S67 and the subsequent steps wherein the heater target temperature is switched to 750° C., to calculate to update the purge air concentration and the purge ratio correction value.

Figure 16:
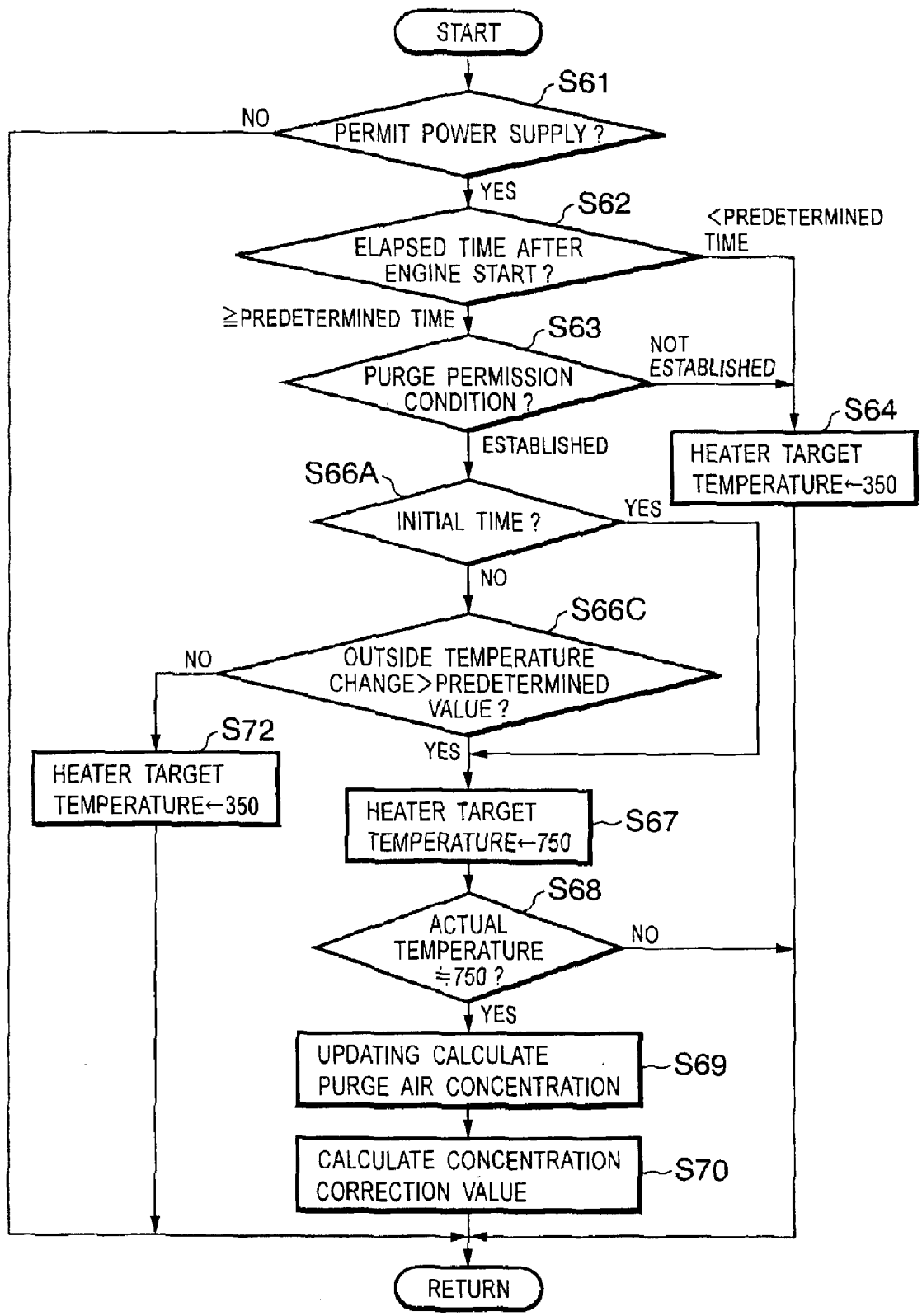
FIG. 16 is a flowchart showing a sixth embodiment of the heater temperature control.

Moreover, a flowchart of FIG. 16 shows an embodiment in which the timing of switching the heater target temperature to 750° C. and calculating to update the purge air concentration and the purge ratio correction value is set to each time when the outside temperature is changed by a predetermined value or more.

That is, in this embodiment, timing in which the operating conditions are changed and the vapor generating amount is increased or decreased is judged as the timing in which the outside temperature is changed by the predetermined value or more, to update the purge air concentration with the heater temperature as 750° C. at each time when the outside temperature is changed by the predetermined value or more.

In the embodiment shown in the flowchart of FIG. 16, at step S66A, it is judged whether or not it is the initial time the purge permission condition is established, and if it is the initial time, control proceeds from step S66A to step S67 wherein the heater target temperature is switched to 750° C. to calculate the purge air concentration and the purge ratio correction value.

Thereafter, the heater target temperature is maintained at 350° C. until it is judged at step S66C that the outside temperature is changed by the predetermined value or more.

Then, if it is judged at step S66C that the outside temperature is changed by the predetermined value or more, control proceeds to step S67 and the subsequent steps wherein the heater target temperature is switched to 750° C. to calculate to update the purge air concentration and the purge ratio correction value.

Incidentally, the constitution may be such that the outside temperature in step S66C is replaced with a fuel temperature or a cooling water temperature, and the heater target temperature is switched to 750° C. at each time the fuel temperature or the cooling water temperature is changed by a predetermined value or more, to calculate to update the purge air concentration and the purge ratio correction value.

Figure 17:
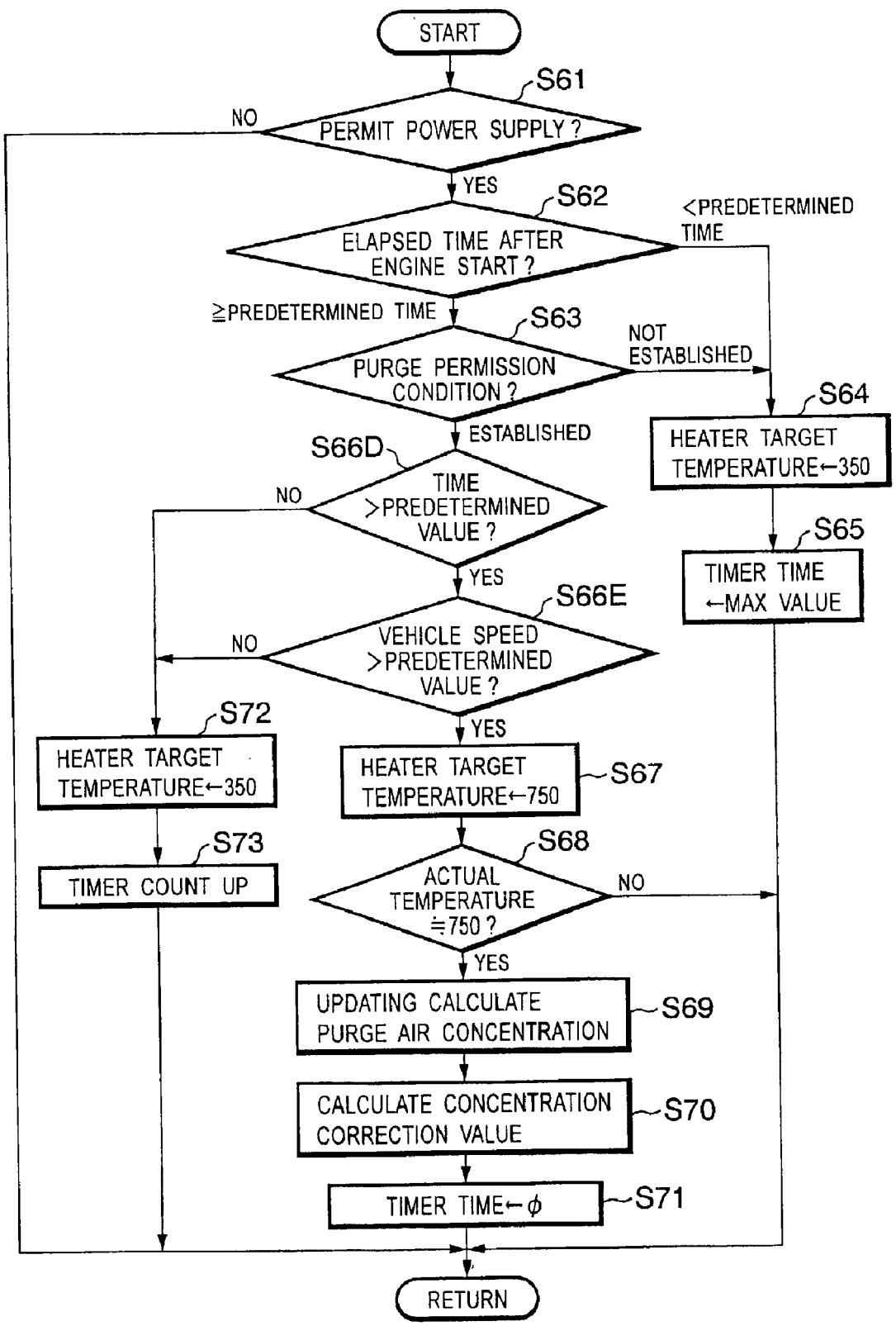
FIG. 17 is a flowchart showing a seventh embodiment of the heater temperature control.

An embodiment shown in a flowchart of FIG. 17 is to calculate to update the purge air concentration at each fixed time measured by the timer TIME in a condition of a predetermined vehicle speed or higher at which, in particular, the purge air concentration is estimated to become rich.

That is, in this embodiment, the purge air concentration is updated with the heater temperature as 750° C. only in the condition of high vehicle speed at which the purge air concentration becomes richer than at normal time.

In the flowchart of FIG. 17, even if it is judged at step S66D that the timer TIME exceeds the predetermined value, the heater target temperature is maintained at 350° C. if it is judged at step S66E that the vehicle speed does not exceed a predetermined value (for example, 90 km/h).

On the other hand, if the vehicle speed exceeds the predetermined value, the heater target temperature is switched to 750° C. at each predetermined time, to calculate to update the purge air concentration and the purge ratio correction value.

Note, the predetermined value to be compared with the timer TIME at step S66D, is set to be shorter than that set at S66 in FIG. 14 at which the heater temperature is periodically set to 750° C. only by the timer TIME.

Further, the vehicle speed in step S66E may be replaced with the fuel temperature or the outside temperature, and the heater target temperature is switched to 750° C. at each predetermined time in the condition in which the fuel temperature or the outside temperature exceeds a predetermined value, to calculate to update the purge air concentration and the purge ratio correction value.

Figure 18:
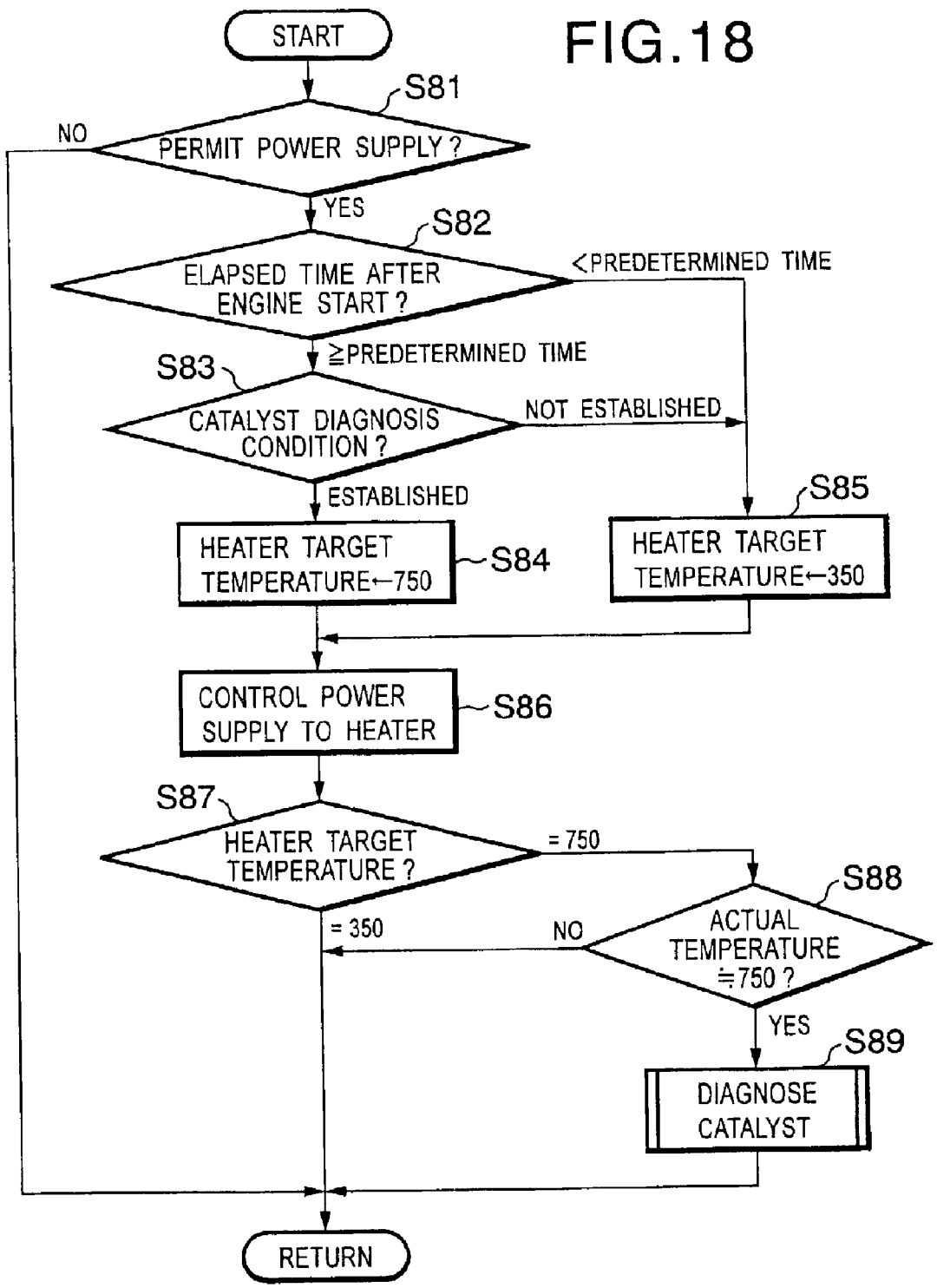
FIG. 18 is a flowchart showing an eighth embodiment of the heater temperature control.

A flowchart of FIG. 18 shows an embodiment in which the heater target temperature is switched according to a request in a catalyst diagnosis.

At step S81, it is judged whether or not the permission condition of the power supply to ceramic heater 27b is established.

If the power supply permission condition is established, control proceeds to step S82 wherein it is judged whether or not the elapsed time t from the start of engine 1 becomes the predetermined time t1 or longer, and if the predetermined time t1 or longer has elapsed, control proceeds to step S83.

At step S83, it is judged whether or not a diagnosis condition of catalyst 8 is established.

The diagnosis condition includes that catalyst 8 is activated, it is the operating condition where there is a little influence even if the air-fuel ratio is shifted for diagnosis, a diagnosis for each one trip has been completed and the like.

If the diagnosis condition of catalyst 8 is established, it is necessary to detect the air-fuel ratio in a wide range based on the output from oxygen sensor 27 for the purpose of diagnosis as described later.

Therefore, control proceeds to step S84 wherein 750° C. is set to the target temperature in the power supply control to ceramic heater 27b.

On the other hand, if the elapsed time t from engine start is shorter than the predetermined time t1, or if the diagnosis condition of catalyst 8 is not established, control proceeds to step S85 wherein the heater target temperature is set to 350° C.

That is, even if the elapsed time from engine start becomes the predetermined time t1 or longer, the heater target temperature is set to 350° C. at a normal time when the catalyst diagnosis is not performed. At this time, since oxygen sensor 27 exhibits the stoichiometric characteristic, the setting of air-fuel ratio feedback correction coefficient is performed even after the engine warm-up based on the rich/lean judgment result, in the air-fuel ratio feedback control using oxygen sensor 27.

At step S86, the power supply to ceramic heater 27b is controlled in accordance with the target temperature set at step S84 or at step S85.

At step S87, it is judged which of 350° C. or 750° C. the target temperature in the power supply control to ceramic heater 27b is set to.

If it is judged at step S87 that the target temperature in the power supply control to ceramic heater 27b is judged to be 750° C. (the second temperature region), control proceeds to step S88.

At step S88, it is judged whether or not the element temperature of oxygen sensor 27 actually reaches around 750° C., and if the element temperature actually reaches around 750° C., control proceeds to step S89 to execute the catalyst diagnosis.

The detail of catalyst diagnosis at step S89 is shown in a flowchart of FIG. 19.

At step S891, an oxygen excess amount or an oxygen lack amount is calculated based on a deviation amount of the air-fuel ratio on the upstream side of catalyst 8 detected by oxygen sensor 27 from the stoichiometric air-fuel ratio, and an intake air flow amount Q corresponding to an exhaust air flow amount.

At next step S892, the calculation result at step S891 is integrated to calculate the stored oxygen amount in the catalyst.

At step S893, it is judged whether or not the output from oxygen sensor 27 indicates the lean air-fuel ratio.

If it is judged at step S893 that the output from oxygen sensor 27 indicates the lean air-fuel ratio, it is judged that the stored oxygen amount in the catalyst at that time is saturated, then control proceeds to step S894.

At step S894, it is judged whether or not the stored oxygen amount at that time exceeds a reference amount.

Then, if the stored oxygen amount exceeds the reference amount, it is judged that catalyst 8 is not deteriorated, and then control proceeds to step S895 wherein it is judged whether or not catalyst 8 is normal.

On the other hand, if the stored oxygen amount is equal to or less the reference amount, it is judged that the oxygen amount capable to be adsorbed is decreased due to the deterioration in oxygen storage capability of catalyst 8, and then control proceeds to step S896 wherein it is judged whether or not catalyst 8 is deteriorated.

The entire contents of Japanese Patent Application No. 2001-343758, filed Nov. 8, 2001 and Japanese Patent Application No. 2001-353242, filed Nov. 19, 2001, priorities of which are claimed, are incorporated herein by reference.

While only selected embodiments have been chosen to illustrate the present invention, it will be apparent to those skilled in the art from this disclosure that various changes and modifications can be made herein without departing from the scope of the invention as defined in the appended claims.

Furthermore, the foregoing description of the embodiments according to the present invention are provided for illustration only, and not for the purpose of limiting the invention as defined in the appended claims and their equivalents.

What is claimed is:

1. An air-fuel ratio control apparatus of an engine, for feedback controlling an air-fuel ratio of combustion mixture of said engine, said apparatus comprising:

an oxygen concentration detector in which a detection signal thereof is changed according to oxygen concentration in engine exhaust air, and said detection signal has a linearity to an air-fuel ratio within a predetermined air-fuel ratio range inclusive of a stoichiometric air-fuel ratio; and a control unit receiving the detection signal from said oxygen concentration detector, to output an air-fuel ratio feedback control signal based on said detection signal, wherein said control unit limits a change in said air-fuel ratio feedback control signal calculated on the basis of said detection signal which is outside a region indicating said linearity so as to be smaller than that in said air-fuel ratio feedback control signal calculated on the basis of said detection signal which is within said region indicating said linearity.

2. An air-fuel ratio control apparatus of an engine according to claim 1, wherein when the detection signal from said oxygen concentration detector is within the region indicating said linearity and also a change speed of said detection signal is a predetermined value or above, said control unit limits the change in said air-fuel ratio feedback control signal to be the same as that when the detection signal from said oxygen concentration detector is outside the region indicating said linearity.

3. An air-fuel ratio control apparatus of an engine according to claim 1,
wherein said control unit switches a limit value of said air-fuel ratio feedback control signal, to limit the change in said air-fuel ratio feedback control signal to be smaller.

4. An air-fuel ratio control apparatus of an engine according to claim 1,
wherein said control unit switches a control gain of said air-fuel ratio feedback control signal, to limit the change in said air-fuel ratio feedback control signal to be smaller.

5. An air-fuel ratio control apparatus of an engine, for feedback controlling an air-fuel ratio of combustion mixture of said engine, said apparatus comprising:
an oxygen concentration detector in which a detection signal thereof is changed according to oxygen concentration in engine exhaust air, and said detection signal has a linearity to an air-fuel ratio within a predetermined air-fuel ratio range inclusive of a stoichiometric air-fuel ratio; and
a control unit receiving the detection signal from said oxygen concentration detector, to output an air-fuel ratio feedback control signal based on said detection signal,
wherein when the detection signal from said oxygen concentration detector is outside a region indicating said linearity, said control unit limits a change in said air-fuel ratio feedback control signal to be smaller than that when the detection signal from said oxygen concentration detector is within said region, and
wherein said control unit switches a step change amount of said air-fuel ratio feedback control signal, to limit the change in said air-fuel ratio feedback control signal to be smaller.

6. An air-fuel ratio control apparatus of an engine, for feedback controlling an air-fuel ratio of combustion mixture of said engine, said apparatus comprising:
an oxygen concentration detector in which a detection signal thereof is changed according to oxygen concentration in engine exhaust air, and said detection signal has a linearity to an air-fuel ratio within a predetermined air-fuel ratio range inclusive of a stoichiometric air-fuel ratio; and
a control unit receiving the detection signal from said oxygen concentration detector, to output an air-fuel ratio feedback control signal based on said detection signal,
wherein when the detection signal from said oxygen concentration detector is outside a region indicating said linearity, said control unit limits a change in said air-fuel ratio feedback control signal to be smaller than that when the detection signal from said oxygen concentration detector is within said region, and
wherein a three-way catalyst is provided in an exhaust pipe of said engine, and
said control unit:
calculates a stored oxygen amount in said three-way catalyst based on the detection signal from said oxygen concentration detector, and
calculates said air-fuel ratio feedback control signal based on a deviation between said stored oxygen amount and a target amount.

7. An air-fuel ratio control method of an engine, for feedback controlling an air-fuel ratio of combustion mixture of said engine using an oxygen concentration detector in which a detection signal thereof is changed according to oxygen concentration in engine exhaust air, and said detection signal has a linearity to an air-fuel ratio within a predetermined air-fuel ratio range inclusive of a stoichiometric air-fuel ratio, said method comprising the steps of:
judging whether or not the detection signal from said oxygen concentration detector is outside a region indicating said linearity; and
limiting a change in said air-fuel ratio feedback control signal calculated on the basis of said detection signal which is outside a region indicating said linearity so as to be smaller than that in said air-fuel ratio control signal calculated on the basis of said detection signal which is within said region indicating said linearity.

8. An air-fuel ratio control method of an engine according to claim 7, further comprising the steps of:
judging whether or not a change speed of said detection signal is a predetermined value or above when the detection signal from said oxygen concentration detector is within the region indicating said linearity; and
limiting the change in said air-fuel ratio feedback control signal when the detection signal from said oxygen concentration detector is within the region indicating said linearity and also the change speed of said detection signal is a predetermined value or above, to be the same as that when the detection signal from said oxygen concentration detector is outside the region indicating said linearity.

9. An air-fuel ratio control method of an engine according to claim 7,
wherein said step of limiting the change in said air-fuel ratio feedback control signal to be smaller, comprises the step of:
switching a limit value of said air-fuel ratio feedback control signal.

10. An air-fuel ratio control method of an engine according to claim 7,
wherein said step of limiting the change in said air-fuel ratio feedback control signal to be smaller, comprises the step of:
switching a control gain of said air-fuel ratio feedback control signal.

11. An air-fuel ratio control method of an engine, for feedback controlling an air-fuel ratio of combustion mixture of said engine using an oxygen concentration detector in which a detection signal thereof is changed according to oxygen concentration in engine exhaust air, and said detection signal has a linearity to an air-fuel ratio within a predetermined air-fuel ratio range inclusive of a stoichiometric air-fuel ratio, said method comprising the steps of:
judging whether or not the detection signal from said oxygen concentration detector is outside a region indicating said linearity; and
limiting a change in said air-fuel ratio feedback control signal to be smaller than that when the detection signal from said oxygen concentration detector is within said region,
wherein said step of limiting the change in said air-fuel ratio feedback control signal to be smaller, comprises the step of:

switching a step change amount of said air-fuel ratio feedback control signal.

12. An air-fuel ratio control apparatus of an engine, for feedback controlling an air-fuel ratio of combustion mixture of said engine, said apparatus comprising:
   an oxygen concentration detector in which a detection signal thereof is changed according to oxygen concentration in engine exhaust air, and said detection signal has a linearity to an air-fuel ratio within a predetermined air-fuel ratio range inclusive of a stoichiometric air-fuel ratio; and
   a control unit receiving the detection signal from said oxygen concentration detector, to output an air-fuel ratio feedback control signal based on said detection signal,
   wherein when the detection signal from said oxygen concentration detector is outside a region indicating said linearity, said control unit limits a change in said air-fuel ratio feedback control signal to be smaller than that when the detection signal from said oxygen concentration detector is within said region,
   wherein a three-way catalyst is provided in an exhaust pipe of said engine, and
   said method further comprises the steps of:
   calculating a stored oxygen amount in said three-way catalyst based on the detection signal from said oxygen concentration detector; and
   calculating said air-fuel ratio feedback control signal based on a deviation between said stored oxygen amount and a target amount.

13. An air-fuel ratio detecting apparatus of an engine, for detecting an air-fuel ratio of combustion mixture of said engine, said apparatus comprising:
   an oxygen concentration detector of which detection signal is changed according to oxygen concentration in engine exhaust air, in which said detection signal is abruptly changed on reaching a stoichiometric air-fuel ratio when an element temperature is within a first temperature region, and said detection signal indicates a linearity to an air-fuel ratio within a predetermined air-fuel ratio range inclusive of the stoichiometric air-fuel ratio when the element temperature is within a second temperature region higher than said first temperature region;
   a heater heating an element of said oxygen concentration detector; and
   a control unit controlling said heater, to switch the element temperature of said oxygen concentration detector to either said first temperature region or said second temperature region,
   wherein said control unit selects either said first temperature region or said second temperature region based on a request in a detection characteristic of air-fuel ratio to control said heater so as to achieve said selected temperature region.

14. An air-fuel ratio detecting apparatus of an engine according to claim 13,
   wherein said control unit judges that said permissible temperature of the element is low under a condition in which a water is adhered to the element of said oxygen concentration detector, to select said first temperature region.

15. An air-fuel ratio detecting apparatus of an engine according to claim 14,
   wherein said control unit judges said water adhered condition, based on an elapsed time from engine start.

16. An air-fuel ratio detecting apparatus of an engine according to claim 13,
   wherein said control unit generally selects said first temperature region and judges rich/lean of air-fuel ratio to the stoichiometric air-fuel ratio based on the detection signal from said oxygen concentration detector, and also
   selects said second temperature region temporarily under a specific condition in which a wide range air-fuel ratio detection is requested, to detect the air-fuel ratio in a wide range based on the detection signal from said oxygen concentration detector.

17. An air-fuel ratio detecting apparatus of an engine according to claim 16,
   wherein a catalyst is provided on a downstream side of said oxygen concentration detector, and
   said specific condition is the one in which a stored oxygen amount of said catalyst is estimated based on the air-fuel ratio, and a deterioration diagnosis of said catalyst is performed based on said estimated stored oxygen amount.

18. An air-fuel ratio detecting apparatus of an engine according to claim 17,
   wherein there is provided a canister collectively adsorbing fuel vapor in a fuel tank, and
   said specific condition is the one in which concentration of purge air purged from said canister is estimated based on the air-fuel ratio, and a purge ratio is controlled based on said estimated stored oxygen amount.

19. An air-fuel ratio detecting method of an engine provided with: an oxygen concentration detector of which detection signal is changed according to oxygen concentration in engine exhaust air in which said detection signal is abruptly changed on reaching a stoichiometric air-fuel ratio when an element temperature is within a first temperature region, and said detection signal indicates a linearity to an air-fuel ratio within a predetermined air-fuel ratio range inclusive of the stoichiometric air-fuel ratio when the element temperature is within a second temperature region higher than said first temperature region; and a heater heating an element of said oxygen concentration detector, said method comprising the steps of:
   judging a request in the element temperature of said oxygen concentration detector;
   controlling said heater in response to the request in the element temperature, to switch the element temperature of said oxygen concentration detector to either said first temperature or said second temperature,
   wherein said step of judging the request in said element temperature comprises the steps of:
   judging a request in a detection characteristic of air-fuel ratio; and
   judging the request in the element temperature based on said request in the detection characteristic.

20. An air-fuel ratio detecting method according to claim 19, wherein said step of judging the permissible temperature comprises the steps of:
   judging whether or not a water is adhered to the element of said oxygen concentration detector; and
   judging that said permissible temperature of the element is low when the water is adhered to the element.

21. An air-fuel ratio detecting method according to claim 20,
   wherein said step of judging the water adhered condition comprises the steps of:

measuring an elapsed time from engine start; and judging whether or not the water is adhered to the element based on said elapsed time.

22. An air-fuel ratio detecting method according to claim 19, wherein said step of judging the request in the detection characteristic of air-fuel ratio comprises the steps of:

selecting a characteristic in which said detection signal indicates the linearity to the air-fuel ratio within said predetermined air-fuel ratio range under a specific condition in which a wide range air-fuel ratio detection is requested; and selecting a characteristic in which said detection signal is abruptly changed on reaching the stoichiometric air-fuel ratio in conditions other than said specific condition.

23. An air-fuel ratio detecting method according to claim 22, wherein there is provided a catalyst on a downstream side of said oxygen concentration detector, said method comprises the steps of:

estimating a stored oxygen amount of said catalyst based on the air-fuel ratio; and diagnosing a deterioration of said catalyst based on said stored oxygen amount, and said step of selecting the characteristic in which the detection signal indicates the linearity to the air-fuel ratio comprises the step of:

judging a condition in which said deterioration diagnosis is performed as said specific condition.

24. An air-fuel ratio detecting method according to claim 22, wherein there is provided a canister collectively adsorbing fuel vapor in a fuel tank, said method comprises the steps of:

estimating concentration of purge air purged from said canister based on the air-fuel ratio; and controlling a purge ratio based on said purge air concentration, and said step of selecting the characteristic in which the detection signal indicates the linearity to the air-fuel ratio comprises the step of:

judging a condition in which said purge ratio is controlled as said specific condition.

* * * * *